US011224706B2

(12) United States Patent
Scott et al.

(10) Patent No.: US 11,224,706 B2
(45) Date of Patent: Jan. 18, 2022

(54) DISPENSER

(71) Applicant: NERUDIA LTD., Liverpool (GB)

(72) Inventors: Kenneth Scott, Liverpool (GB); David Jones, Liverpool (GB); Thomas Sudlow, Liverpool (GB); Alfred Madden, Liverpool (GB); Christopher Lord, Liverpool (GB)

(73) Assignee: Nerudia Ltd., Liverpool (GB)

( * ) Notice: Subject to any disclaimer, the term of this patent is extended or adjusted under 35 U.S.C. 154(b) by 615 days.

(21) Appl. No.: 15/354,177

(22) Filed: Nov. 17, 2016

(65) Prior Publication Data
US 2017/0135398 A1 May 18, 2017

(30) Foreign Application Priority Data

Nov. 17, 2015 (GB) ...................................... 1520271
Aug. 4, 2016 (GB) ...................................... 1613460

(51) Int. Cl.
A24F 47/00 (2020.01)
A61M 15/06 (2006.01)
(Continued)

(52) U.S. Cl.
CPC ............ *A61M 15/06* (2013.01); *A24F 40/10* (2020.01); *A24F 40/40* (2020.01); *A24F 40/42* (2020.01);
(Continued)

(58) Field of Classification Search
None
See application file for complete search history.

(56) References Cited

U.S. PATENT DOCUMENTS 3,729,116 A    4/1973  Green
3,811,590 A *  5/1974  Hall, Jr. ............... B65D 50/067
                                                    215/207
(Continued)

FOREIGN PATENT DOCUMENTS

CN    103418062    12/2013
CN    203723443    7/2014
(Continued)

OTHER PUBLICATIONS

English translation of Motobayashi et al. (WO2012070107A1) (Year: 2012).*
(Continued)

*Primary Examiner* — Michael J Felton
*Assistant Examiner* — Katherine A Will
(74) *Attorney, Agent, or Firm* — Sheppard Mullin Richter & Hampton LLP

(57) ABSTRACT

The present invention relates to a dispenser for dispensing a liquid, comprising: a reservoir for storing a liquid to be dispensed; a manually operative pump arrangement disposed at a first end region of the reservoir; a conduit extending from the pump arrangement to a second end region of the reservoir distal the first end region, the conduit configured for communicating reservoir contents from the second end region to the pump arrangement; a dispense conduit extending from the pump arrangement and comprising a dispense aperture at an end region thereof, the dispense aperture in liquid communication with the pump arrangement; and an open ended tube extending in a direction away from the pump arrangement and configured to surround the dispense conduit, wherein the open ended tube extends to a position such that the open end thereof is at least coterminous with an dispense aperture end of the dispense conduit and actuation of the pump arrangement causes transfer of (Continued)

reservoir contents from the reservoir to the dispense aperture end of the dispense conduit.

22 Claims, 17 Drawing Sheets

(51) Int. Cl.
| | |
|---|---|
| B05B 11/00 | (2006.01) |
| B65B 31/00 | (2006.01) |
| A24F 40/42 | (2020.01) |
| A24F 40/48 | (2020.01) |
| A24F 40/485 | (2020.01) |
| A24F 40/10 | (2020.01) |
| A24F 40/40 | (2020.01) |
| B67D 7/02 | (2010.01) |
| B67D 7/42 | (2010.01) |
| A61M 11/04 | (2006.01) |
| A24F 15/015 | (2020.01) |
| A24F 40/00 | (2020.01) |

(52) U.S. Cl.
CPC .......... *A24F 40/48* (2020.01); *A24F 40/485* (2020.01); *A61M 11/042* (2014.02); *B05B 11/0097* (2013.01); *B65B 31/003* (2013.01); *B67D 7/0205* (2013.01); *B67D 7/0288* (2013.01); *B67D 7/42* (2013.01); *A24F 15/015* (2020.01); *A24F 40/00* (2020.01); *A61M 2209/045* (2013.01)

(56) References Cited

U.S. PATENT DOCUMENTS

| | | | |
|---|---|---|---|
| 4,173,858 A | 11/1979 | Cassia | |
| 5,358,149 A | 10/1994 | O'Neill | |
| 2005/0016622 A1 | 1/2005 | Risch | |
| 2008/0067193 A1 | 3/2008 | Powers | |
| 2008/0241255 A1* | 10/2008 | Rose et al. | A61K 9/14 424/489 |
| 2010/0147899 A1* | 6/2010 | Nardi | B65D 47/18 222/420 |
| 2010/0242975 A1 | 9/2010 | Hearn | |
| 2014/0283946 A1* | 9/2014 | Kribs | B65D 47/06 141/2 |
| 2015/0245666 A1* | 9/2015 | Memari | A24F 15/12 131/329 |
| 2015/0257447 A1 | 9/2015 | Sullivan | |
| 2015/0313287 A1 | 11/2015 | Verleur | |
| 2015/0335074 A1* | 11/2015 | Leung | A24F 47/008 |
| 2016/0023227 A1* | 1/2016 | Scott et al. | B05B 11/0056 |
| 2016/0332754 A1* | 11/2016 | Brown | B65B 3/10 |
| 2018/0036754 A1 | 2/2018 | Scott | |

FOREIGN PATENT DOCUMENTS

| | | |
|---|---|---|
| CN | 204377931 | 6/2015 |
| CN | 204682530 | 10/2015 |
| EP | 1244486 | 10/2002 |
| EP | 2801272 | 11/2014 |
| EP | 2977108 | 1/2016 |
| EP | 3100956 | 12/2016 |
| GB | 928589 | 6/1963 |
| GB | 2524296 | 9/2015 |
| JP | 2004290473 A | 10/2004 |
| JP | 2005148343 A | 6/2005 |
| RU | 2311859 | 12/2007 |
| WO | 2008121610 | 10/2008 |
| WO | 2009071643 | 6/2009 |
| WO | 2012070107 | 5/2012 |
| WO | 2014139609 | 9/2014 |
| WO | 2014195859 | 12/2014 |
| WO | 2015128667 | 9/2015 |

OTHER PUBLICATIONS

Japanese Patent Application No. 2018-525585, Office Action dated Oct. 20, 2020, with English translation, 25 pages.

Lauterbach, John H., et al., "Suggested Protocol for Estimation of Harmful and Potentially Harmful Constituents in Mainstream Aerosols generated by Electronic Delivery Systems (ENDS)", presented at SOT, San Francisco, California, http://cigtoxdoc.ehost-services113.com/sot2012poster1860aspresented.pdf, Mar. 10-16, 2012, 5 pages.

* cited by examiner

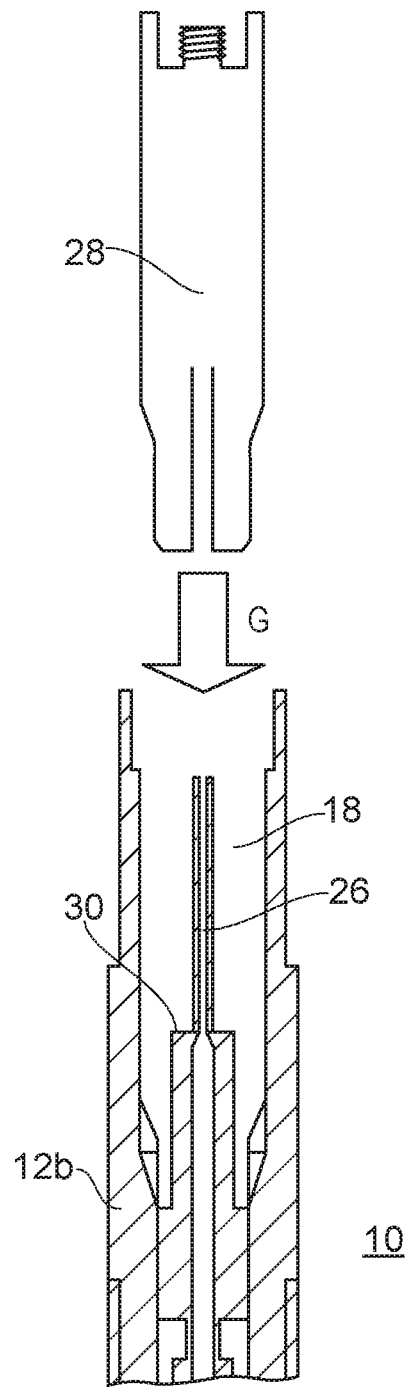
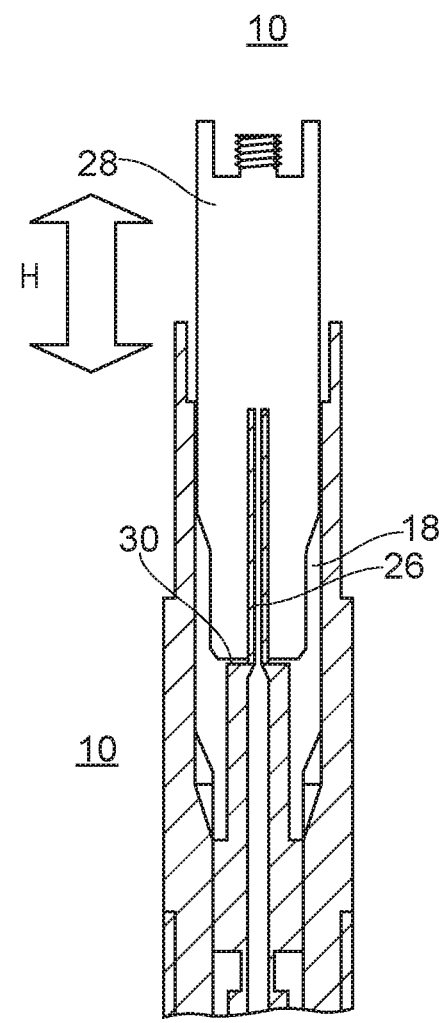
FIG. 13g
FIG. 13h

DISPENSER

RELATED APPLICATIONS

This application claims the priority benefit of Great Britain Application 1520271.6, filed on Nov. 17, 2015 and Great Britain Application 1613460.3, filed on Aug. 4, 2016 in the Great Britain Patent Office, the disclosures of which are hereby incorporated by reference in their entirety.

FIELD

The present invention relates to a dispenser, in particular but not exclusively to a dispenser for dispensing a liquid.

BACKGROUND

A smoking-substitute device is an electronic device that permits the user to simulate the act of smoking by producing an aerosol mist or vapour that is drawn into the lungs through the mouth and then exhaled. The inhaled aerosol mist or vapour typically bears nicotine and/or other flavourings without the odour and health risks associated with traditional smoking and tobacco products. In use, the user experiences a similar satisfaction and physical sensation to those experienced from a traditional smoking or tobacco product, and exhales an aerosol mist or vapour of similar appearance to the smoke exhaled when using such traditional smoking or tobacco products.

A smoking-substitute device generally uses heat and/or ultrasonic agitation to vaporize a solution comprising nicotine and/or other flavouring, propylene glycol and/or glycerine-based base into an aerosol mist of vapour for inhalation. A person of ordinary skill in the art will appreciate that the term "smoking-substitute device" as used herein includes, but is not limited to, electronic nicotine delivery systems (ENDS), electronic cigarettes, e-cigarettes, e-cigs, vaping cigarettes, pipes, cigars, cigarillos, vaporizers and devices of a similar nature that function to produce an aerosol mist or vapour that is inhaled by a user. Some electronic cigarettes are disposable; others are reusable, with replaceable and refillable parts.

Smoking-substitute devices typically resemble a traditional cigarette and are cylindrical in form with a mouthpiece at one end through which the user can draw the aerosol mist or vapour for inhalation. These devices usually share several common components: a power source such as a battery, a reservoir for holding the liquid to be vaporized, a vaporization component for atomizing and/or vaporizing the liquid and to thereby produce an aerosol mist and/or vapour, and control circuitry operable to actuate the vaporization component responsive to an actuation signal from a switch operative by a user or configured to detect when the user draws air through the mouthpiece by sucking or inhaling.

The reservoir may be either a replaceable or refillable container that is coupled to, or located in, the main body of the smoking-substitute device and that is typically made of a resilient plastic material such as high-density polypropylene. The reservoir generally contains a wicking material in which the liquid is stored but may just be a storage space without any wicking material. Once the replaceable or refillable reservoir is emptied it must either be replaced or refilled.

Replaceable type reservoirs are typically provided in the form of a pre-filled cartridge that can be securely and removably engaged to, or within, the cylindrical main body of the smoking-substitute device. These reservoir and vaporization elements may also be integrated into a single component commonly known as a "cartomizer" that may be disposable or refillable. Additionally, replaceable type reservoirs may also be integrally formed with the mouthpiece.

In order to fit a replaceable type reservoir to, or within, the main body of a smoking-substitute device, features of the main body are configured to engage with complementary features formed on a portion of the reservoir to securely and removably couple the reservoir to the main body of the smoking substitute device and to thereby prevent the accidental or unintended separation of the reservoir from the smoking-substitute device. These complementary features typically secure the reservoir to the main body of the smoking-substitute device with a close or interference fit and the fitting step causes a portion of the reservoir to pierce the reservoir to permit liquid to be dispensed.

Alternatively, and most commonly, users utilise refillable type reservoirs. Typically, the refillable reservoir of the smoking-substitute device is refilled by dispensing liquid from a dispenser that commonly resembles the small dropper bottles used for dispensing eye drops. Refill dispensers are preferred principally for their low cost.

The ingredients of the liquid for producing the aerosol mist or vapour in smoking-substitute devices vary widely, but typically include water and flavourings in a propylene glycol and/or glycerol base. Nicotine may also be included in solutions intended to fulfil a nicotine replacement role, without the harmful products associated with tobacco smoke.

A person of ordinary skill in the art will appreciate that the term "liquid" as used herein, may include, but is not limited to, any liquids, gels, powders and gases together with liquids comprising mixtures of liquids, gels, powders and gases that are capable of being atomized or vapourized whether or not using heat and/or ultrasonics. Additionally, the term "liquid" as used herein may also include, but is not limited to, powders capable of being entrained in a fluid flow, for example an airflow.

When refilling the reservoir from a dispenser, the user typically drips liquid from the outlet liquid-dispensing tip of the dispenser into an inlet of the reservoir by squeezing the walls of the dispenser. Any wicking material in the reservoir then absorbs the dispensed liquid or the space in the reservoir is simply filled with the dispensed liquid. Since the diameter of the inlet on the smoking-substitute device is typically quite narrow it is important that the liquid-dispensing tip of the dispenser is correctly aligned to prevent spillage.

Additionally, the user must correctly judge the pressure with which the dispenser should be squeezed to controllably expel liquid from the liquid-dispensing tip. Furthermore, as the user releases the bottle air is sucked in through the liquid-dispensing tip to replace the volume of liquid that has just been dispensed, but can also suck recently dispensed liquid from the reservoir and back into the dispenser causing droplets of liquid to be expelled inadvertently from the reservoir. Consequently, this refill technique is cumbersome and typically results in spillages of oily liquid, which has an oily consistency, and so some users have found that utilizing a syringe to draw liquid from the outlet of the dispenser before injecting it through the inlet of the reservoir is more convenient. However, such a procedure utilises a sharp such as a hypodermic needle arrangement and puts a user at risk of injury from the sharp piercing the skin and also contamination of their skin and potentially sub-dermal layers with the liquid due to its presence on the needle.

A method of refilling the reservoir of a smoking-substitute device from a dispenser is disclosed in US 2014/0283946 A1 (Kribs, et al). This published patent application describes a cap that fits over the liquid-dispensing tip of a standard eyedropper type refill dispenser. The cap has a first portion with a bore into which the liquid-dispensing tip of a standard bottle is received, and an inner annular wall that is threaded, such that a gap is disposed between the liquid-dispensing tip and the threaded portion of the inner annular wall. When liquid is to be dispensed into the reservoir to refill the reservoir, the first portion of the cap is screwed onto a reciprocal threaded outer portion of the smoking-substitute device. When fully engaged the first portion of the cap is substantially sealed against the inlet of the reservoir of the smoking-substitute device to permit liquid to flow between the dispenser and the reservoir and alleviate leakage. Additionally, it is difficult to determine the amount of liquid input to the reservoir, unless of course the reservoir walls are transparent. Even so, if it were desired to input only a specific amount of liquid into the reservoir a user will still find it difficult even if the walls of the reservoir were transparent because the nature of a squeezable bottle for dispensing liquid into the reservoir results in an inaccurate volume of liquid being dispensed, not least because the "suck back" effect of the bottle to replace the volume of liquid dispensed with air.

The popularity and use of smoking-substitute devices has grown rapidly in the past few years. Although originally marketed as an aid to assist habitual smokers wishing to quit traditional smoking and tobacco products, consumers are increasingly viewing smoking substitute devices as desirable lifestyle accessories. This has caused concern that smoking-substitute devices may be becoming fashionable in certain sections of the population, and that their use may as a consequence be attractive to children and young adults who may subsequently graduate to traditional smoking and tobacco products.

There is also significant on-going scientific debate about the long-terms effects on health from the prolonged use of smoking-substitute devices and the inhalation of atomized mists and/or vapours comprising nicotine constituents. However, it is generally accepted that the levels of toxicants consumed by users of such smoking-substitute devices is a fraction of those consumed by users of traditional smoking and tobacco products. See, for example, John H. Lauterbach et al, "*Suggested Protocol for Estimation of Harmful and Potentially Harmful Constituents in Mainstream Aerosols generated by Electronic Delivery Systems (ENDS)*", presented at SOT, San Francisco, Calif., Mar. 10-16, 2012 (http://cigtoxdoc.ehost-services113.com/sot2012poster1860aspresented.pdf) and hereby incorporated by reference. Nonetheless, the health issues connected with the prolonged use of smoking-substitute devices is increasingly receiving negative press coverage and is the subject of much political debate. One area of particular concern is the quality and provenance of many liquids presently available of the market. Concerns raised, particularly by the medical profession, also focus on the lack of information available to consumers regarding the use of smoking-substitute devices and associated liquids that prevent them from making informed decisions regarding their use.

To address safety and quality concerns relating to traditional smoking and tobacco products, the World Health Organisation (WHO) published the Framework Convention on Tobacco Control (FCTC) in May 2003. The FCTC provisions are intended to regulate the sale and marketing of tobacco and tobacco-alternative products, the disclosure of information relating to such products, the packaging and labelling of such products, and the advertising of such products. These provisions are binding on the European Union (EU) and its' Member States who have adopted a set of guidelines for the implementation of the FCTC provisions by consensus during a series of subsequent conferences. Although, the FCTC did not anticipate the market for smoking-substitute devices, the governments of several Member States have decided that it would be appropriate to adapt the current legislation resulting from the FCTC and that relates to traditional smoking and tobacco products to incorporate such smoking-substitute devices.

In Europe efforts to adapt the existing legislation followed the publication of various reports and advice received from the Scientific Committee on Newly Identified Health Risks (SCENIHR) on smokeless tobacco products and tobacco additives. The European Parliament and Council of the European Union has proposed repealing Directive 2001/37/EC and replacing it with Directive 2014/40/EU on Apr. 3, 2014 (Tobacco Products Directive or TPD). The TPD proposes regulations applicable to smoking-substitute devices that will:

limit the risks of inadvertent exposure to nicotine by setting maximum sizes for refill reservoirs, containers, tanks, and cartridges (Article 20.3(a))

limit the concentration of nicotine in the liquid to 20 mg/ml (Article 20.3(b)).

prohibit the use of certain additives in the liquid (Article 20.3(c))

require that only high-purity ingredients are used in the manufacture of liquids (Article 20.3(d)).

require that all ingredients (except nicotine) do not pose a risk to human health in heated or unheated form (Article 20.3(e))

require that all smoking-substitute devices deliver doses of nicotine at consistent levels under normal conditions of use (Article 20.3(f))

require that all products include child and tamper-proof labelling, fasteners and opening mechanisms (Article 20.3(g)).

require that all products meet certain safety and quality standards and to ensure that products do no break or leak during use or refill (penultimate and final sentences, paragraph 41 of the recitals).

One area of particular concern to consumers and regulators is that the increased availability of smoking-substitute devices and refill liquids in supermarkets and other outlets may create a health risk particularly if they fall into the hands of children. Although these liquids typically comprise nicotine in concentrations of less than or equal to 3.6% of the liquid that is generally regarded as safe and merely a stimulant, nicotine in much higher concentration has in the past been used as an insecticide and in concentrations of 50-100 mg can be harmful to humans. Nonetheless, solutions comprising nicotine are treated as toxic by postal services and carriers, and so appropriate precautions are required when handling and storing nicotine in bulk.

Aspects and embodiments of the invention were devised with the foregoing in mind.

SUMMARY

Viewed from a first aspect there is provided a dispenser for dispensing a liquid, comprising:

a reservoir for storing a liquid to be dispensed;

a manually operative pump arrangement disposed at a first end region of the reservoir;

a conduit extending from the pump arrangement to a second end region of the reservoir distal the first end region, the conduit configured for communicating reservoir contents from the second end region to the pump arrangement;

a dispense conduit extending from the pump arrangement and comprising a dispense aperture at an end region thereof, the dispense aperture in liquid communication with the pump arrangement; and an open ended tube extending in a direction away from the pump arrangement and configured to surround the dispense conduit, wherein the open ended tube extends to a position such that the open end thereof is at least coterminous with a dispense aperture end of the dispense conduit and actuation of the pump arrangement causes transfer of reservoir contents from the reservoir to the dispense aperture end of the dispense conduit.

Such a dispenser provides an integrated reservoir and dispense pump arrangement in which the dispense conduit may be protected from inadvertent contact, for example by a user, thereby inhibiting the likelihood of contamination of the dispense conduit. Inhibiting contamination of the dispense conduit is particularly important if the dispenser is used for dispensing contents to be consumed by human beings, for example a medicament or a smoking substitute vapour for ingestion or inhalation by a human being.

In one or more embodiments the open ended tube extends to a position beyond the dispense aperture end of the dispense conduit thereby enhancing protection of the dispense conduit from inadvertent contact.

In one or more embodiments the dispense conduit is configured to interface with a complementary arrangement in the container to be filled to deliver reservoir contents into the container. Such an interface between the dispense conduit and a container to be filled may reduce the likelihood of spillage and/or contamination of the reservoir contents during transfer from the dispense conduit to the container to be filled. In a particular embodiment, the dispense conduit is configured to penetrate into a container to be filled to deliver reservoir contents into the container. Penetration into the container to be filled further reduces the likelihood of spillage and contamination of the reservoir contents as they are transferred to the container. Penetration of the dispense conduit into the container provides for delivery of the reservoir contents from the dispense conduit into the container storage cavity thereby avoiding spillage of the reservoir contents during filling.

In a particularly convenient one or more embodiment, the dispense conduit is configured to pierce a membrane of the container to be filled to protrude into the container to be filled to deliver reservoir contents into the container. Such a piercing arrangement is mechanically straightforward and may for example comprise a dispense conduit configured in a similar manner to that of a hypodermic needle. In such one or more embodiments, inhibiting inadvertent contact with the dispense conduit becomes more important than with a non-sharp dispense conduit in order to avoid pinprick or "stick" injury to a user and/or body fluid contamination, such as blood contamination, of the dispense conduit.

Suitably, one or more embodiments are further configured to receive a cap to close the open ended tube, such as a child safety cap. Further protection of the dispense conduit by a cap is particularly important for an embodiment having a sharp dispense conduit. Optionally, an exterior wall and/or interior wall of the open ended tube may be configured for engagement with a portion of the cap. The exterior wall and/or interior wall may comprise engagement formations configured for engagement with complementary engagement formations of the cap. Further optionally, there may be provided a plug member, a portion of which is configured for engagement with the interior wall of the open ended tube. The plug member may comprise engagement formations configured to receive complementary engagement formations of a removal device. The plug member may be removable from the dispenser, when engaged to the removal device, by a pulling action exerted on the removal device. Optionally, the removal device may comprise a container operative with the dispenser for filling the container.

Typically, the pump arrangement is resiliently biased towards a closed position. This may facilitate single-handed operation and reduce the likelihood of leakage when the pump dispenser is not in use. Additionally, such a bias requires a positive pressure to operate the pump arrangement thereby reducing the likelihood of inadvertent actuation and dispensing of the reservoir contents.

In one or more embodiments, the pump arrangement comprises an abutment surface configured to engage with a complementary surface of a container to be filled and wherein application of a force to the abutment surface actuates the pump arrangement. In such one or more embodiments, a container to be filled may be brought into contact with the abutment surface and a force applied to the container to be filled by a user to actuate the pump arrangement. With such a configuration, contact by the user with the dispense conduit and/or pump arrangement is further inhibited by use of the container to be filled as an intermediate member for actuating the pump arrangement. Typically, application of the force is against the resilient bias.

In one or more embodiments, the open ended tube is profiled so as to guide a container to be filled into engagement with the dispense conduit. Such one or more embodiments assist in location of the dispense conduit with the interface formation of a container to be filled thereby avoiding spillage or wastage of reservoir contents. Suitably, the open ended tube is profiled so as to provide a transition fit for engagement of a container to be filled for reciprocal movement of the container to be filled with respect to the open ended tube. Such a transition fit assists in controllably guiding a container to be filled in a reciprocal motion within the open ended tube for effecting actuation of the pump arrangement through contact of respective abutment surfaces of the pump arrangement. Moreover, the container to be filled may be positively located in the open ended tube.

In one or more embodiments, the inner wall of the open ended tube is profiled so as to guide a container to be filled. Insertion of a container to be filled into the open ended tube provides for detail of profiling to be interior to the open ended tube thereby providing an uninterrupted outer surface of the open ended tube. Such an uninterrupted outer surface may assist in the fitting of a cap over the open end of the open ended tube and/or improve the exterior aesthetics of the open ended tube.

In a particularly convenient one or more embodiments, the open ended tube is profiled so as to receive a mouthpiece for a smoking substitute device. In such a one or more embodiments, the open ended tube may be profiled to provide a complementary cross-section, such as for a mouthpiece for a smoking substitute device. Profiling the open ended tube with a certain configuration limits the insertion of containers to be filled to those containers that can fit within the profile, thereby providing a mechanism for inhibiting the use of containers to be filled not intended for use with the dispenser. Profiling may be sufficiently detailed, so as to substantially restrict use of containers to be filled to those having an exact complementary configuration, in particular complementary cross-sectional configuration, to the open ended tube.

Profiling of the open ended tube may also provide a mechanism by which actuation of the pump and thereby dispensing of reservoir contents may only be achieved by use of a suitably shaped member, such as a suitably shaped container to be filled, thereby avoiding inadvertent actuation of the pump and dispensing of the reservoir contents.

Additionally or optionally, the open ended tube may be configured with a locking or a positive engagement mechanism configured to permit a reciprocal movement of the container to be filled when engaged therewith. Additionally or optionally, the pump arrangement may comprise a locking or positive engagement mechanism, for example as part of and/or associated with the abutment surface, interoperable with a complementary mechanism on the container to be filled to avoid inadvertent separation of the container to be filled from the pump arrangement.

In one or more embodiments, a surface of the open ended tube is coated with an antibacterial coating, for example Microban™. This is particularly beneficial where the container to be filled comprises a mouth piece which is inserted into the open ended tube as the exterior of the mouthpiece is cleaned at is inserted into and taken from the open ended tube.

Suitably, the pump mechanism dimensions are configured to deliver a measured dose of reservoir contents for a full pump stroke length. Delivery of such a measured dose is particularly useful where the reservoir contents comprise a medicament. It is also useful where the measured dose is an equally divided amount of the volume of the container to be filled storage region since a user can then actuate the pump a particular number of times to reliably fill storage region. Optionally, a measured dose of reservoir contents for a full pump stroke length may be around 0.25 ml. If the container to be filled comprises a cartomiser (which may, typically, have a reservoir volume of around 2 ml), then it will be appreciated that the pump would require eight full pump stroke length actuations to completely fill the reservoir of the cartomiser from empty. Of course, the full pump stroke length may be configured to deliver other measured doses in other optional arrangements.

To assist in measuring a stroke length the dispenser may be configured to provide feedback indicative of reaching a maximum stroke length, wherein the feedback may be one or more of tactile, visual and audio feedback.

Viewed from a second aspect, there is provided a container operative with the dispenser as described above for filling the container, the container comprising:

a storage cavity for storing reservoir contents dispensed to the container from the dispenser;

an interface formation configured to receive the dispense conduit of the dispenser configured to open a conduit between the storage cavity and pump arrangement to permit transfer of reservoir contents from the pump arrangement to the storage cavity responsive to actuation of the pump arrangement; and wherein the interface formation is disposed in an interface section of the container configured to fit to the open ended tube in order for the dispense conduit to engage with the interface formation.

In one or more embodiments, the interface formation comprises a rupturable membrane which is particularly suited to use with a dispenser having a sharp dispense conduit. Advantageously, the rupturable membrane comprises a self-sealing material, for example silicone, which obviates the need to provide a cap over a ruptured membrane to avoid leakage from the container to be filled due to the ruptured membrane. In particular, the membrane may be made entirely of silicone.

Suitably, the interface section is configured to be insertable into the open ended tube and in particular is configured to form a transition fit with the open ended tube. A transition fit assists in controllably guiding the interface section into the open ended tube such that it may interface with the dispense conduit and also in controllably guiding reciprocal motion of the interface section within the open ended tube for actuation of the pump arrangement.

In one or more embodiments, the interface section comprises an abutment surface configured to contact a complementary abutment surface of the pump arrangement of the dispenser such that reciprocal movement of the container in the open ended tube may actuate the pump arrangement. Thus, the container may be contacted by a user in order to actuate the pump arrangement thereby decreasing the likelihood of a user coming into contact with the dispense conduit or pump arrangement due to the intermediary provided by the interface section.

The interface section may comprise formations complementary to formations in the open ended tube and/or pump arrangement for providing positive engagement therewith in order to inhibit inadvertent separation of the container from the dispenser during operation.

The interface section typically comprises a hollow member at one end of which is the interface formation such that in use a dispense conduit can enter into the hollow member to reach the interface formation.

Suitably, the container may be configured as a container for a nicotine vapour precursor liquid for a smoking substitute device, for example configured as a cartomiser. In embodiments in which the container is configured for a smoking substitute device such as a cartomiser, it is particularly convenient for the interface section to be configured as a mouthpiece. However, the interface section may be configured as a mouthpiece for use with containers other than for smoking substitute devices.

Optionally, the container may be configured for engagement with a plug member located in the open ended tube of the dispenser. This can enable the plug member to be removed from the dispenser by exerting a pulling action on the container, relative to the dispenser, to pull the plug member from the open ended tube of the dispenser. Further optionally, the container may comprise engagement formations configured for engaging complementary engagement formations of the plug member. This may enable the plug member to be securely attached to the container to allow removal of the plug member from the dispenser.

Viewed from a third aspect, there is provided a kit of parts for forming an assembly for filling a container, comprising a dispenser as described above and a container as described above. Such a kit of parts may be provided to a consumer packaged together for the consumer's convenience.

Viewed from a fourth aspect, there is provided a kit of parts for forming a dispenser as described above, comprising:

a hollow tube closed at one end and configured at a position intermediate the closed-end and open-end to provide a support for a manually operative reciprocal pump arrangement, the hollow tube configured to form a reservoir between the position and closed end for storing contents to be dispensed;

a manually operative reciprocal pump arrangement;

a dip tube coupleable to the pump arrangement; and a dispense conduit coupled to the pump arrangement.

Such a kit of parts is a useful collection of components for assembling a dispenser.

BRIEF DESCRIPTION OF THE DRAWINGS

One or more embodiments in accordance with aspects of the present invention will be described, by way of example only, and with reference to the following drawings in which:

FIGS. 13a to 13h are cross-sectional side view illustrations of the dispenser according to one or more embodiments of the present invention during a process for removal of a safety cap, the additional safety cap and a filling process.

DETAILED DESCRIPTION OF THE INVENTION

Figure 1:
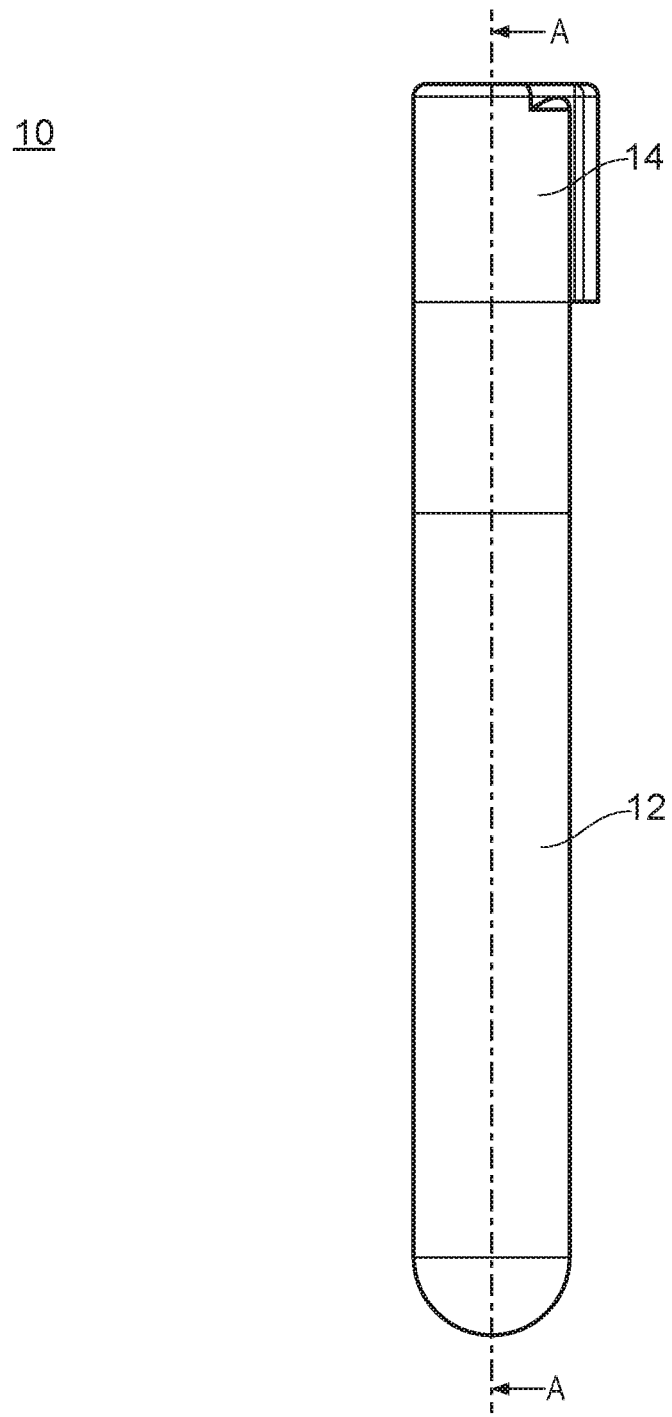
FIG. 1 is a side view illustration of a dispenser according to one or more embodiments of the present invention.

FIG. 1 shows a dispenser 10 for dispensing a liquid. The dispenser 10 can be used to fill or re-fill containers, such as, for example, cartomisers for e-cigarette devices.

The dispenser 10 comprises an elongate, hollow, cylindrical housing 12, which is closed at a first end and open at a second, opposite end, and a cap 14 for closing off the second, open end.

Figure 2:
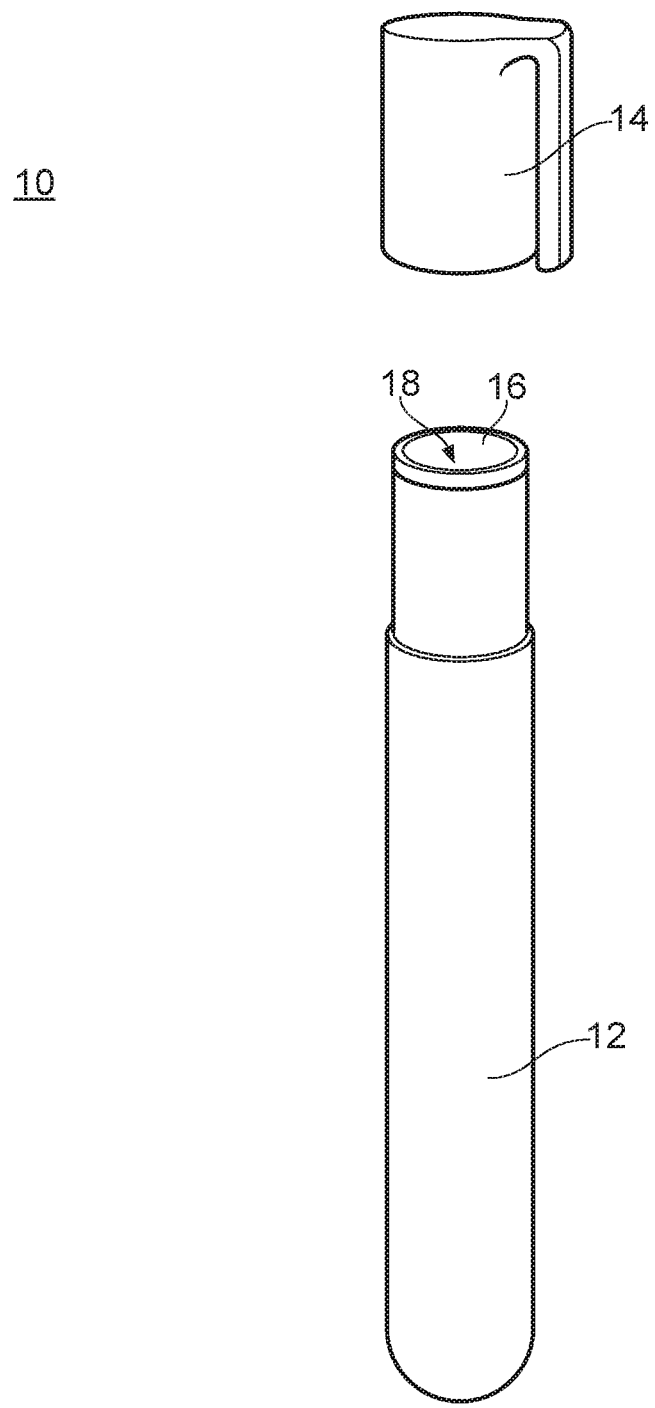
FIG. 2 is a perspective side view illustration of the dispenser of FIG. 1 showing the cap removed.

FIG. 2 shows the dispenser 10 with the cap 14 removed from the housing 12 to expose an aperture 16. Aperture 16, located at the second, open end of housing 12, is configured for receiving a container to be filled and forms an open end of open ended tube 18. The open ended tube 18 is disposed within the housing 12.

When the cap 14 is removed, an end of a container to be filled can be inserted into the open ended tube 18 of the dispenser 10 via the aperture 16.

Figure 3:
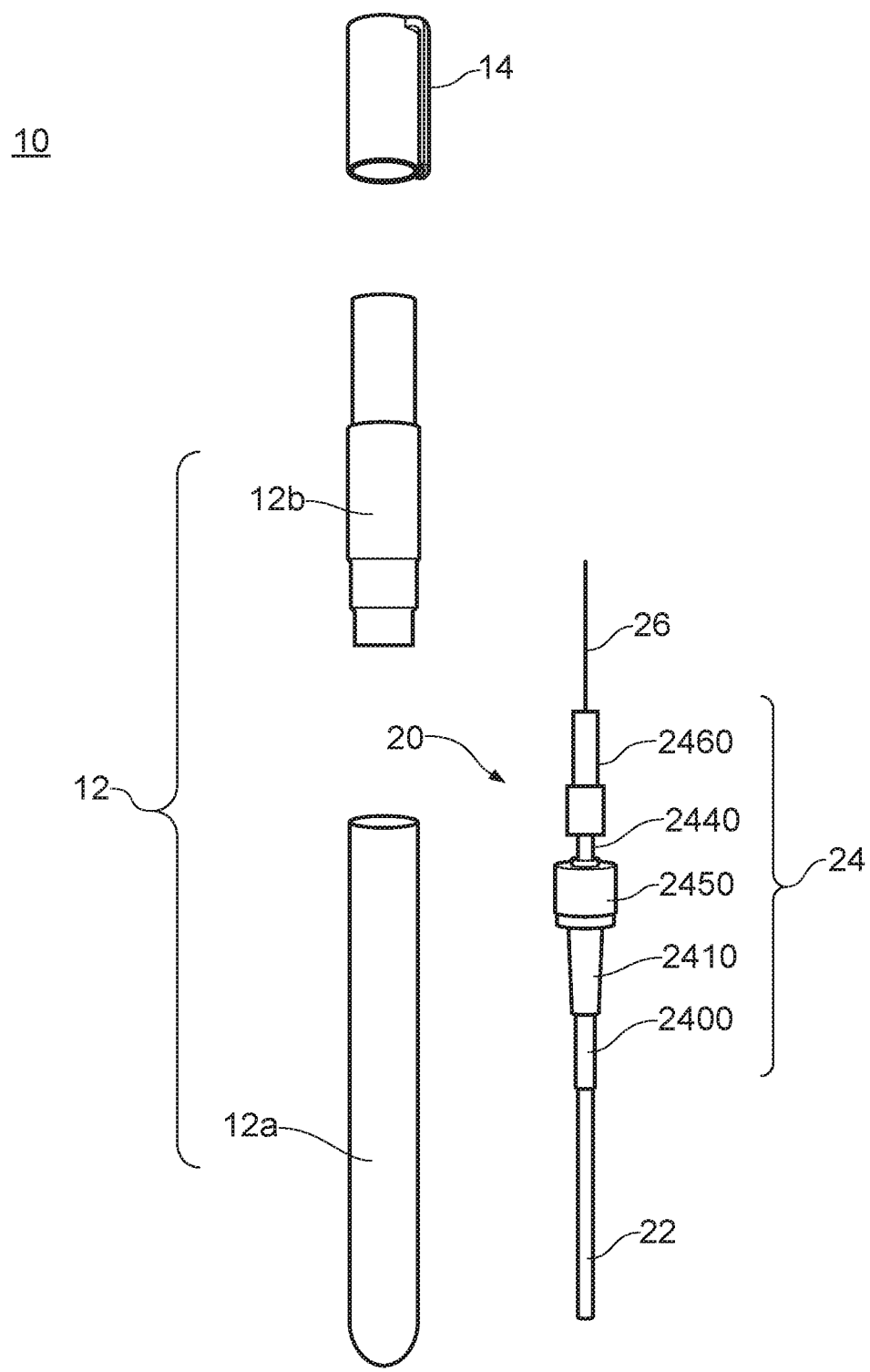
FIG. 3 is an exploded side view illustration of the dispenser according to one or more embodiments of the present invention.

FIG. 3 illustrates, in exploded form, the elements of dispenser 10, i.e. housing 12, which is formed of a reservoir portion 12a and a dispense conduit housing portion 12b, cap 14 and a pump device 20.

The pump device 20 comprises an intake conduit 22 in fluid communication with a pump arrangement 24. Pump arrangement 24 is configured for location at, adjacent, or about a first end of the reservoir portion 12a and is in fluid communication with a dispense conduit 26.

Intake conduit 22 (also known as a "dip tube") extends from the pump arrangement 24 so that, when the pump device 20 is located within housing 12, the intake conduit 22 extends to a second end of the reservoir portion 12a distal the first end. The intake conduit 22 is configured for communicating contents in the reservoir portion 12a from the second end thereof to pump arrangement 24.

The intake conduit 22 comprises a notch across its walls (not shown in FIG. 2, but see feature 32 in FIGS. 7 and 10) to ease suction of liquid from the second end of the reservoir portion 12a.

Dispense conduit 26, such as, for example, a dispense tip, extends from the pump arrangement 24 and comprises a dispense aperture (not shown) at an end thereof. The dispense aperture is in fluid communication with the pump arrangement 24.

When pump device 20 is located within housing 12, the open ended tube (not shown in FIG. 3) extends in a direction away from the pump arrangement 24 and is configured to surround the dispense conduit 26. The open ended tube extends to a position such that the open end thereof is at least coterminous with the dispense aperture end ("tip") of the dispense conduit 26 and actuation of the pump arrangement 24 causes transfer of reservoir contents from the reservoir portion 12a to the dispense aperture end of the dispense conduit 26.

The pump arrangement 24 comprises valve seat element 2400, a hollow cylindrical member 2410, an operating rod 2440, a body portion 2450 and a pump actuator 2460. The pump actuator 2460 is in fluid communication with body portion 2450 by way of operating rod 2440, and valve seat element 2400 is in fluid communication with body portion 2450 by way of hollow cylindrical member 2410. The valve seat element 2400 is in fluid communication with intake conduit 22 and the pump actuator 2460 is in fluid communication with the dispense conduit 26. Thus, a fluid passage is provided through the pump arrangement to provide a fluid passage from a remote end of the intake conduit 22, via the pump arrangement, to a remote end of the dispense conduit 26.

Figure 4:
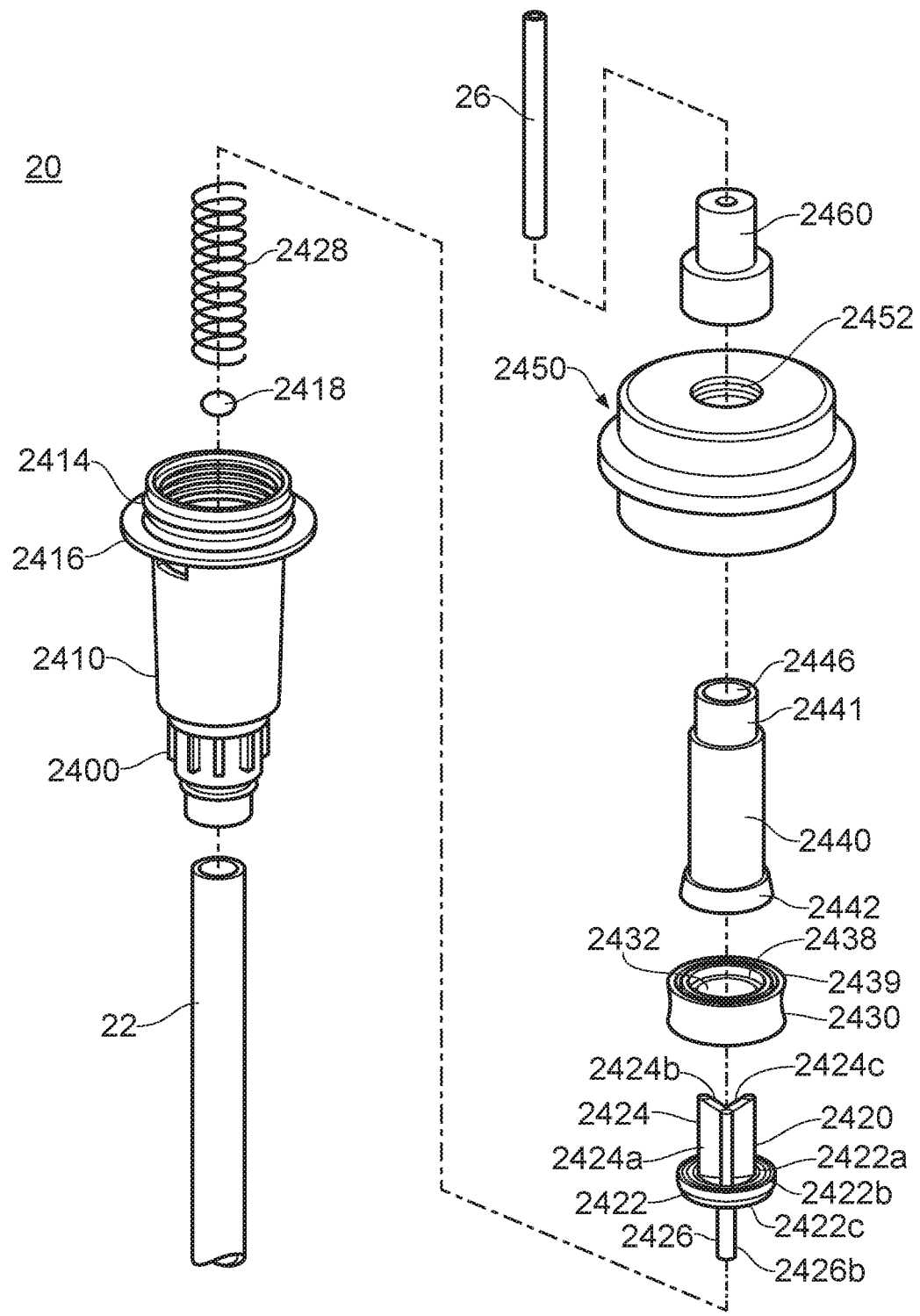
FIG. 4 is an exploded view illustration of a pump device for use in the dispenser according to one or more embodiments of the present invention.
Figure 5:
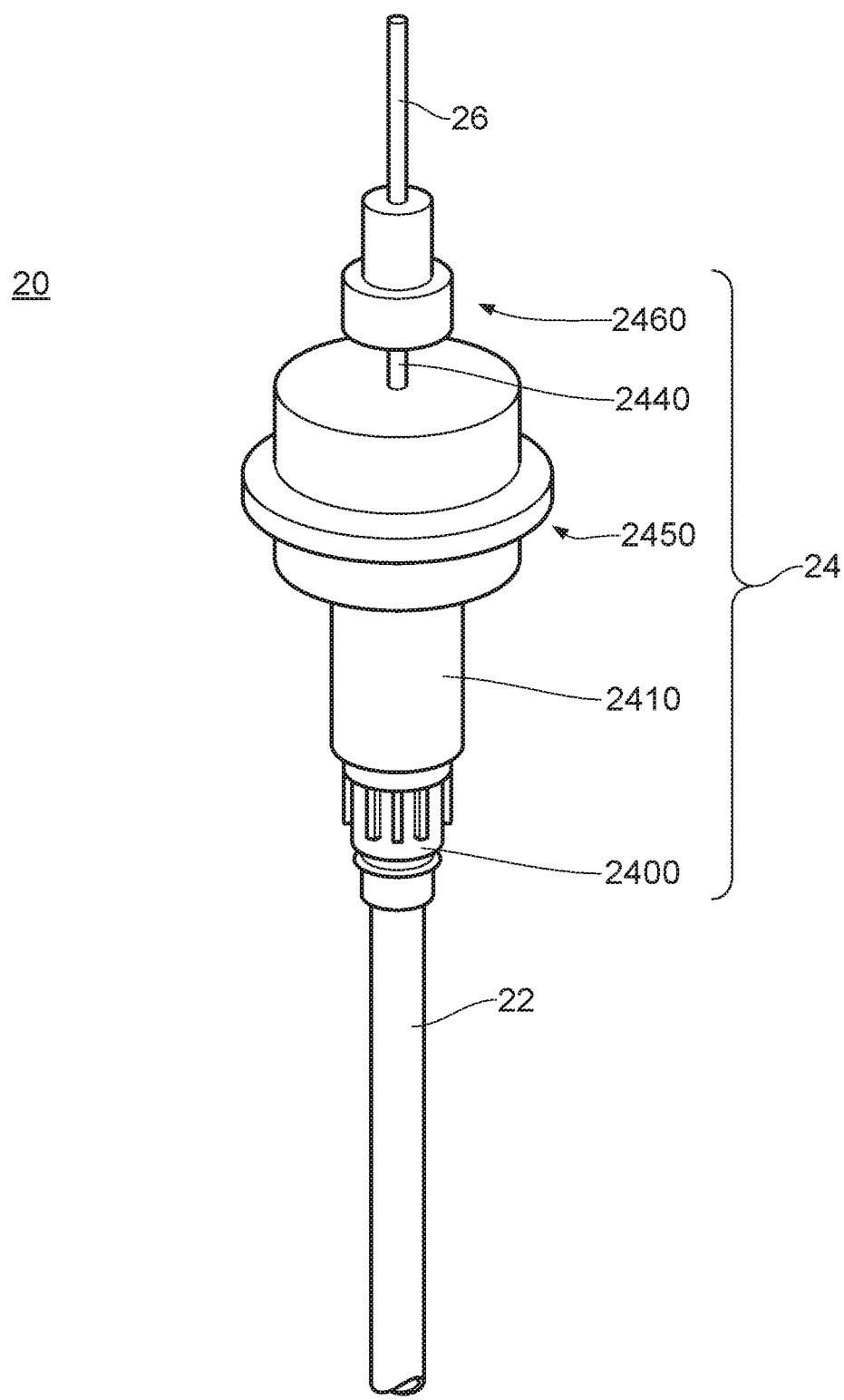
FIG. 5 is a perspective view illustration of the pump device illustrated in FIG. 4.
Figure 6:
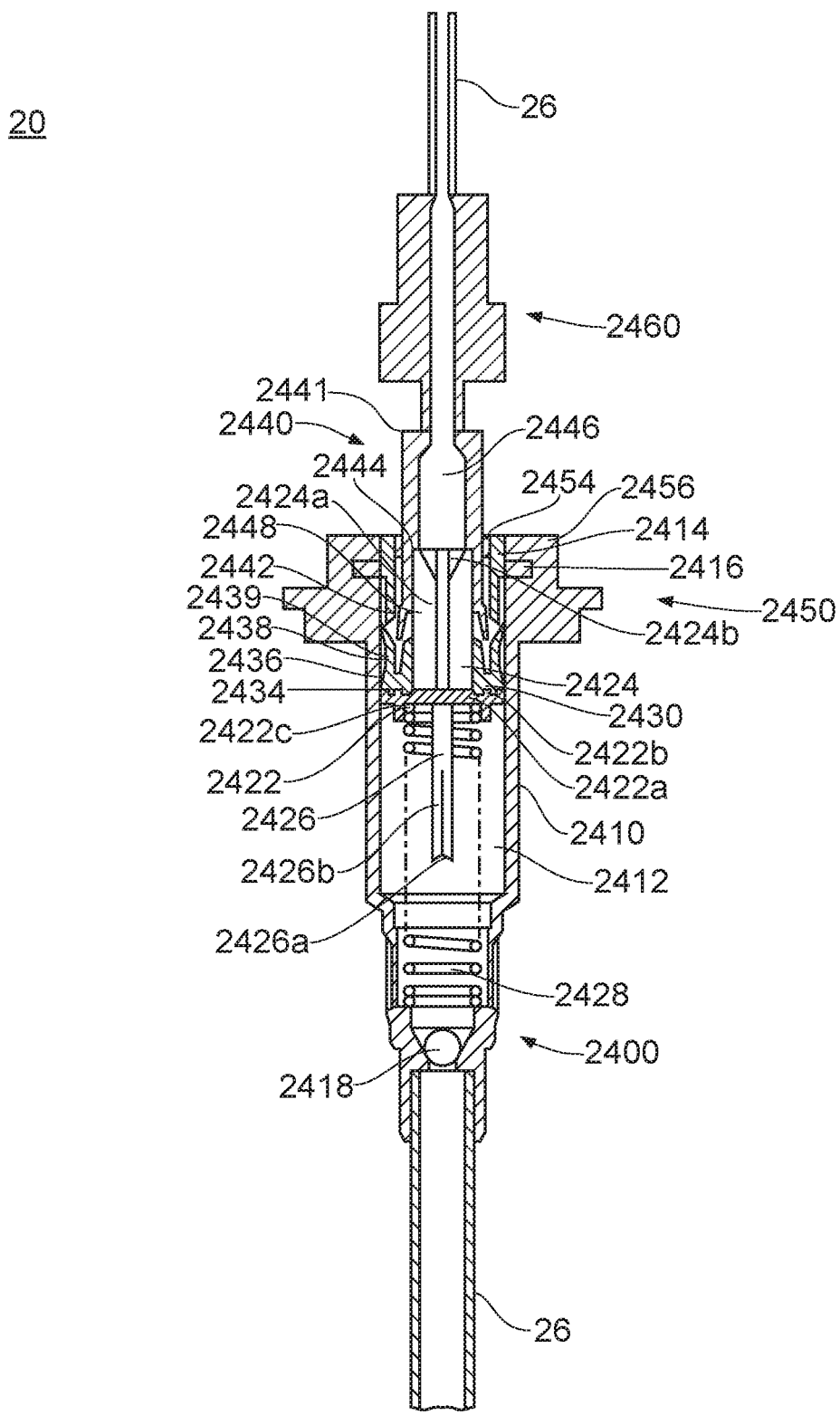
FIG. 6 is a cross-section side view illustration of the pump device illustrated in FIGS. 4 and 5.

Referring now to FIGS. 4 to 6, a pump device 20 suitable for use in a dispenser according to one or more embodiments of the present invention is shown. It will be apparent to those skilled in the art that the pump device 20 illustrated in FIGS. 4 to 6 is merely one example of many suitable types of pump device that could be employed in the dispenser of an embodiment of the present invention.

Pump device 20 comprises intake conduit 22 coupled to valve seat element 2400, which is coupled to hollow cylindrical member 2410. The pump device further comprises an upper valve 2420, a piston member 2430, operating rod 2440, a body portion 2450, and a pump actuator 2460. Cylindrical member 2410 has mounted thereunder the valve seat element 2400 and the intake conduit 22 to be placed in reservoir portion 12a of dispenser 10 and includes a reservoir chamber 2412, a top engaging portion 2414, an annular flange 2416 positioning thereon body portion 2420 to be seated against seat portion 12c, which is a flange disposed around the interior of reservoir portion 12a at said first end thereof. A lower portion of the cylindrical member 2410 is configured for coupling to said valve seat element 2400 in which is located a ball 2418

Upper valve 2420 includes a body portion 2422 having a bottom positioning ring 2422c and two top concentric annular grooves 2422a, 2422b of triangular cross-section, an upper engaging medium 2424 having three upward rectangular wings 2424a respectively having three top inner triangular indentations 2424b to facilitate passing the liquid from three passages 2424c defined by wings 2424a to operating rod 2440, and a downward engaging rod 2426 having a bottom end 2426a split into three fingers 2426b. A compression spring 2428 is positioned in cylindrical member 2410 and mounted between positioning ring 2422c and valve seat element 2400.

Piston 2430 includes a through hole 2432, two concentric bottom annular teeth 2434, 2436 respectively engageable with grooves 2422a, 2422b, a top inner annular indentation 2438 and a top outer annular indentation 2439 and is sleeved in cylindrical member 2410 to be movable along the inner wall thereof.

Operating rod 2440 is hollow and includes a top end 2441, a bottom end having a bottom annular projection 2442 engageable in inner indentation 2438 when operating rod 2440 is pressed downward, and a through hole which includes a shoulder surface 2444 defining thereabove an upper hole 2446 and thereunder a lower hole 2448 receiving therein the upper portion of upper engaging medium 2424 bearing against shoulder surface 2444.

Body portion 2450 includes a through hole 2452, an annular engaging piece 2454 of inverted L-shaped cross-section securely, but moveably receiving therein operating rod 2440, and an engaging top 2456 fixed to top engaging portion 2414.

Figure 10:
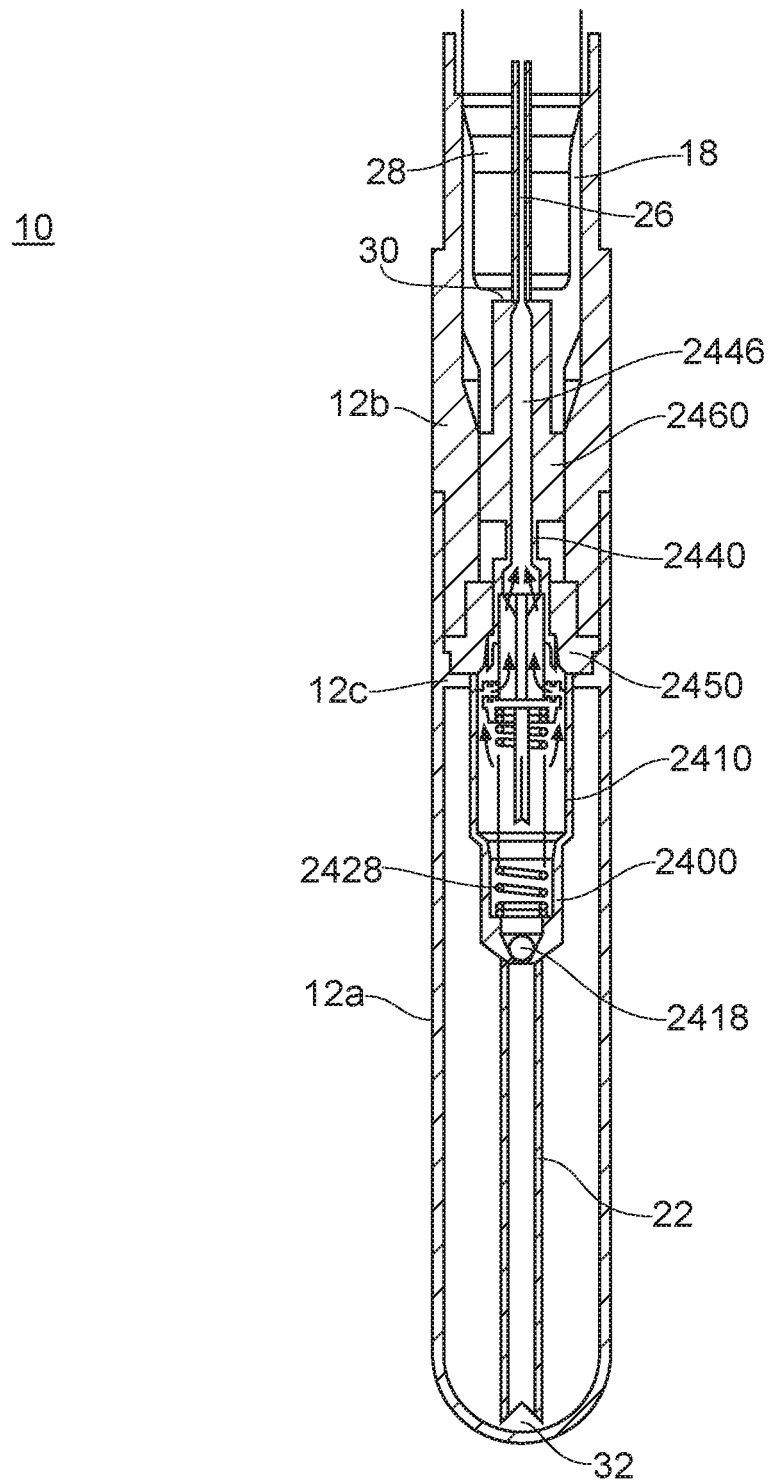
FIG. 10 is a cross-sectional side view illustration of the dispenser according to one or more embodiments of the present invention during a filling process.

In operation, as shown in FIG. 10, when pump actuator 2460 and operating rod 2440 are pressed downward, operating rod 2440 will disengage upper valve 2420 from piston member 2430 to thus connect reservoir chamber 2412 with lower hole 2448 before bottom annular projection 2442 matches with inner indentation 2438. If pump actuator 2460 and operating rod 2440 are further pressed downward, piston 2430 will be moved downward accordingly and thus the air/or liquid in reservoir chamber 2412 will pass through passages 2424c, hole 2446, pump actuator 2460 and dispense conduit 26 to be discharged (denoted by the arrows in the figure). After pump actuator 2460 and operating rod 2440 reach their lowest positions and are released, compression spring 2428 will again match annular teeth 2434, 2436 against annular grooves 2422a, 2422b respectively and displace upward piston 2430 to thus form a vacuum in reservoir chamber 2412 to in turn allow ball 2418 to leave a valve seat in valve seat element 2400 to suck from intake conduit 22 the liquid in the reservoir portion 12a into reservoir chamber 2412. If pump actuator 2460 and operating rod 2440 are pressed downward again, the liquid in reservoir chamber 2412 will be communicated through the conduit through pump actuator 2460 and discharged through dispense conduit 26.

Figure 7:
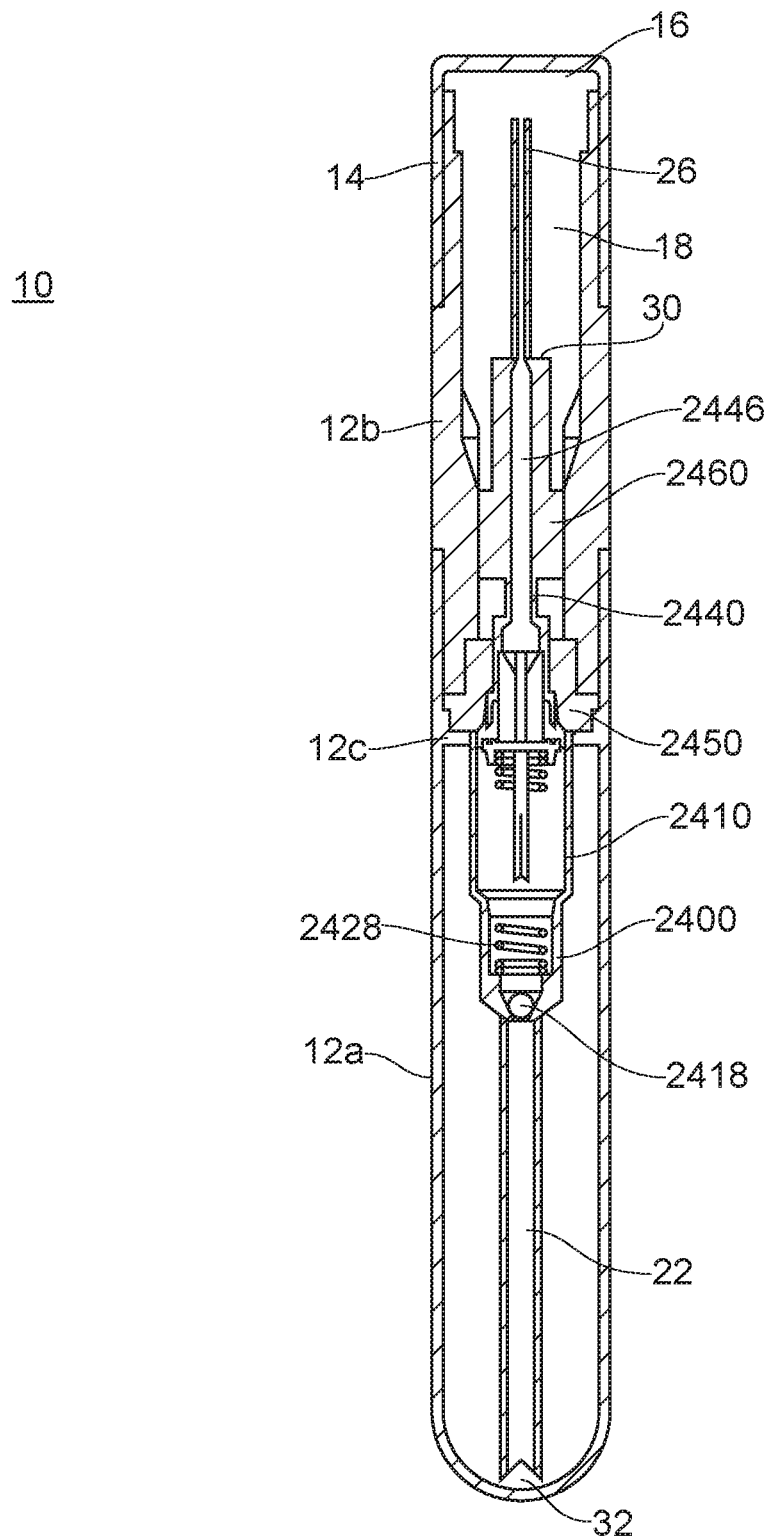
FIG. 7 is a cross-sectional side view illustration of the dispenser according to one or more embodiments of the present invention as viewed along line A-A of FIG. 1.

The assembled dispenser 10 can be seen in cross section view in both FIGS. 7 and 10, both of which illustrates the dispenser 10 as viewed in cross section along line A-A of FIG. 1.

FIG. 7 illustrates the dispenser 10 in a non-use state and FIG. 10 (as described above) illustrates the dispenser during a stage of operation.

As can be seen in FIG. 10, dispense conduit 26 extends through an aperture in the container 28 to be filled and into a reservoir of the container 28.

Figure 8:
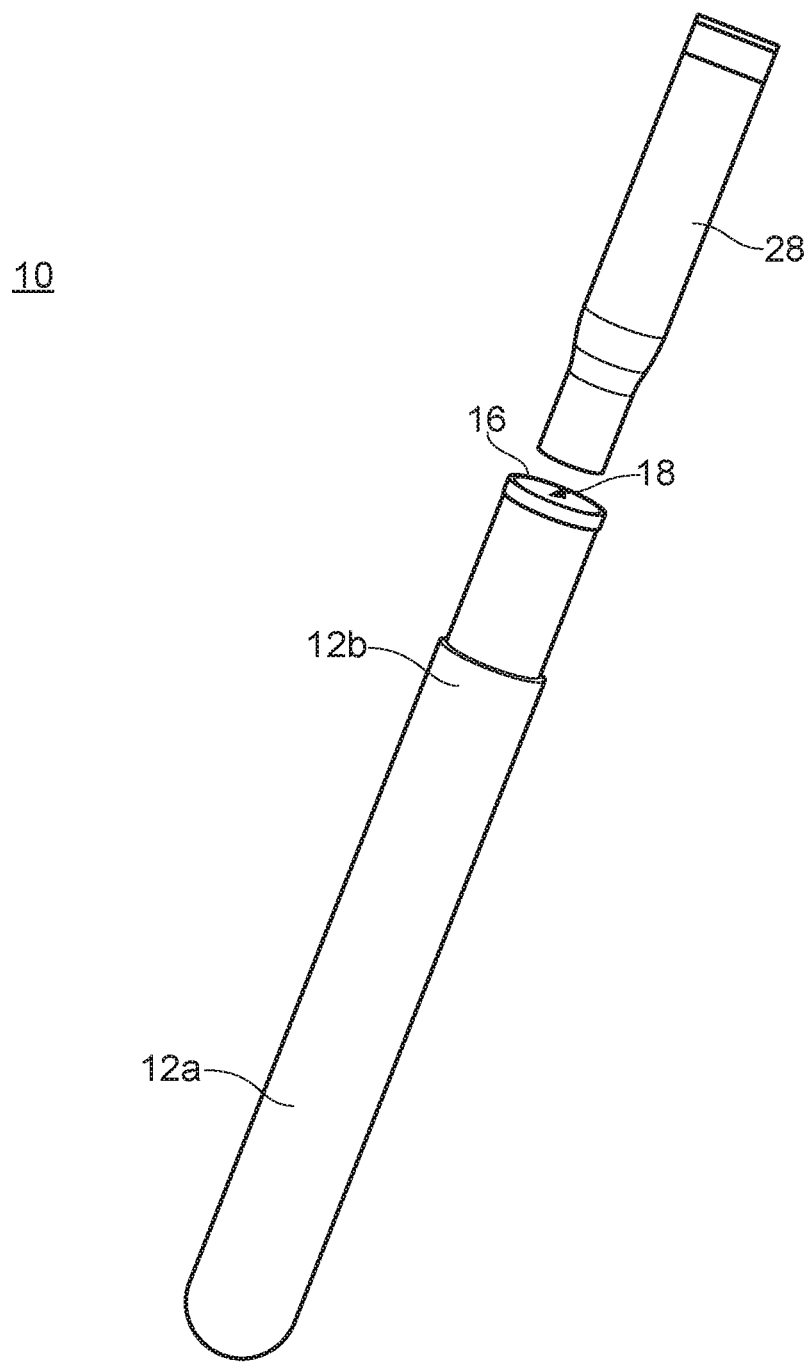
FIG. 8 is a perspective side view illustration of the dispenser according to one or more embodiments of the present invention and a container to be filled.

FIG. 8 is similar to FIG. 2 in that it shows the dispenser 10 with the cap 14 removed from the housing 12 to expose aperture 16. In this figure, a container 28 to be filled is located adjacent aperture and is disposed for insertion into aperture 16 to extend into open ended tube 18.

Figure 9:
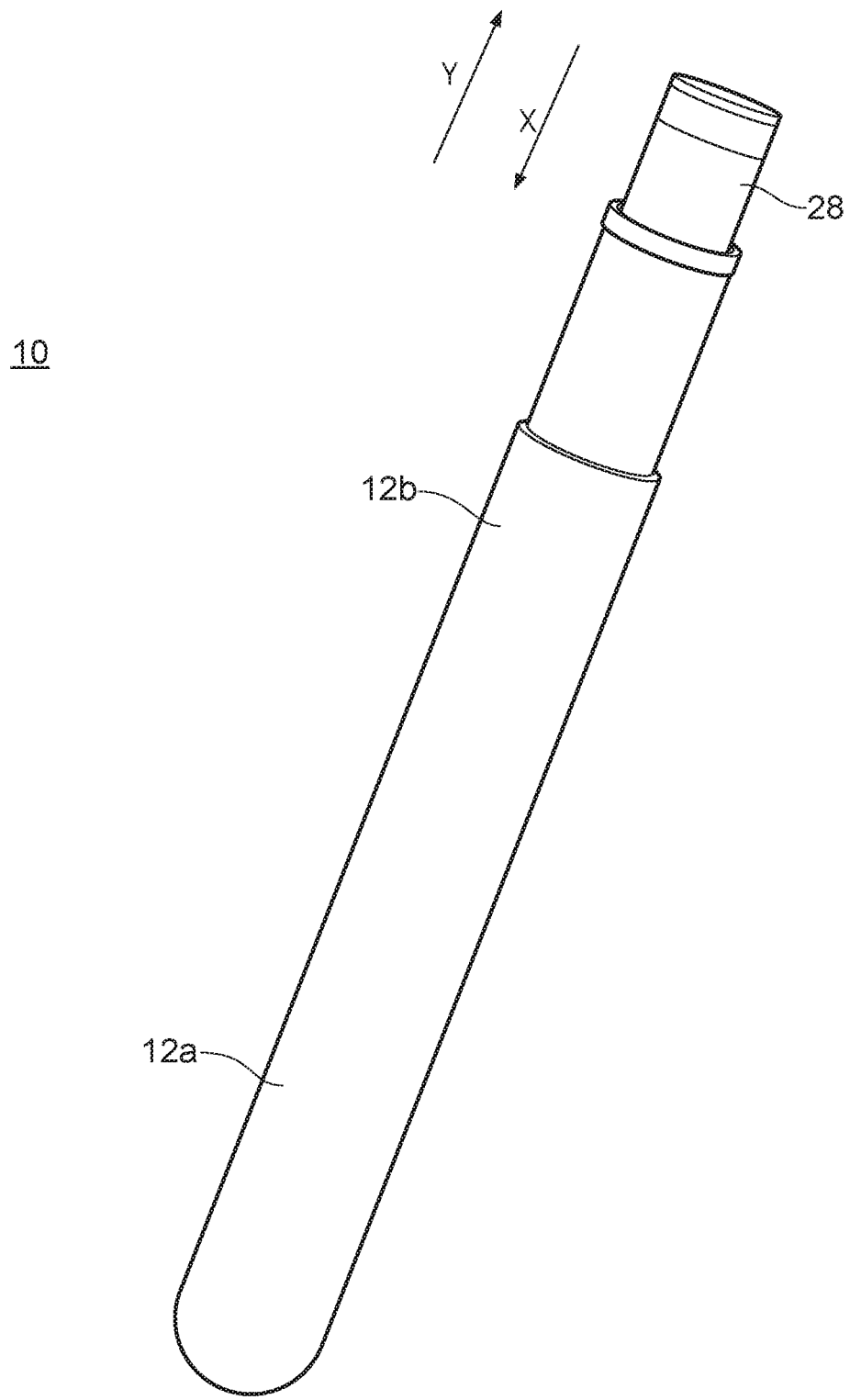
FIG. 9 is a perspective side view illustration of the dispenser according to one or more embodiments of the present invention with the container to be filled located therein.

FIG. 9 shows the container 28 to be filled with a portion thereof located within dispenser 10.

The container 28 can be filled with liquid contained in the reservoir portion 12a of housing 12 by exerting a force (in the direction denoted by arrow X in the figure) on the exposed end of the container 28 to urge container 28 from a rest position into the dispenser 10. This action causes an end of the container 28 within the dispenser to abut an end of the pump arrangement (not shown in FIG. 9, but see feature 30 in FIG. 10). Continued depression of the container 28 relative to the dispenser 10 against the action of compression spring within the pump arrangement causes actuation of the pump arrangement until the pump actuator is in a fully depressed position. Actuation of the pump arrangement causes liquid to be communicated via the dispense conduit (not shown), which extends through an aperture of the container 28 into a reservoir thereof, to deliver liquid to the reservoir of the container 28.

Upon release of the depressing force, the compression spring within the pump arrangement urges the container 28 from the fully depressed position towards the rest position (i.e. in the direction denoted by arrow Y in the figure).

The container 28 can be moved through a number of depression and release cycles in order to fill the container. However, in an optional arrangement, the pump device 20 may be such that the container can be filled by way of a single depression and release cycle. The pump arrangement dimensions may be such that each depression and release cycle delivers a measured dose of contents such as a medicament in order to avoid inadvertent over medication by a user.

Figure 11:
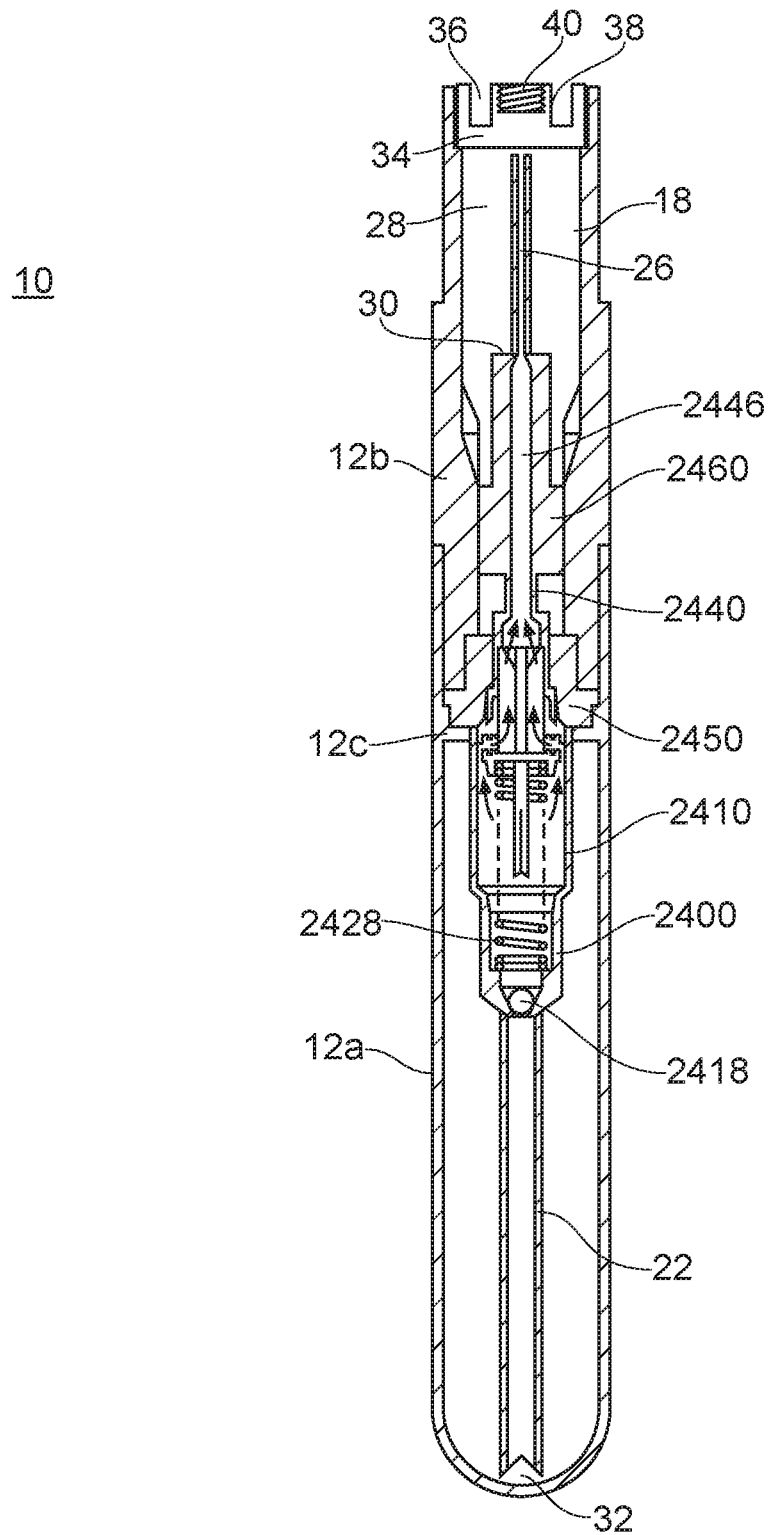
FIG. 11 is a cross-sectional side view illustration of the dispenser according to one or more embodiments of the present invention comprising an additional safety cap.

In further one or more embodiments of the present invention illustrated in FIG. 11, the dispenser 10 comprises, in addition to cap 14, a plug 34 for closing off the second, open end of the dispenser. Plug 34 is configured to be located in open ended tube 18 for closing off aperture 16. The plug 34 comprises features configured to engage with complementary features formed on an internal wall of the open ended tube 18 at, or adjacent, aperture 16 to securely and removably locate the plug 34 within the open ended tube 18 and to thereby prevent the accidental or unintended separation of the plug 34 from the open ended tube 18. These complementary features typically secure the plug 34 within the open ended tube 18 (i.e. to the internal wall of the open ended tube 18) with a close, or interference, or push fit.

The plug 34 comprises a disc-shaped element, which includes an annular recess 36 in a top surface thereof. The annular recess 36 surrounds a shaft 38 in which is provided an engagement formation (e.g. a helically threaded bore 40 as illustrated in FIG. 11) configured to receive a complementary engagement formation of a removal device.

The plug 34 provides an additional feature (i.e. additional to cap 14) for inhibiting inadvertent contact with the dispense conduit 26.

In the further one or more embodiments illustrated in FIG. 11, an end of a container to be filled can be inserted into the open ended tube 18 of the dispenser 10 via the aperture 16 only when both the cap 14 has been removed and the plug 34 has been removed.

Figure 12A:
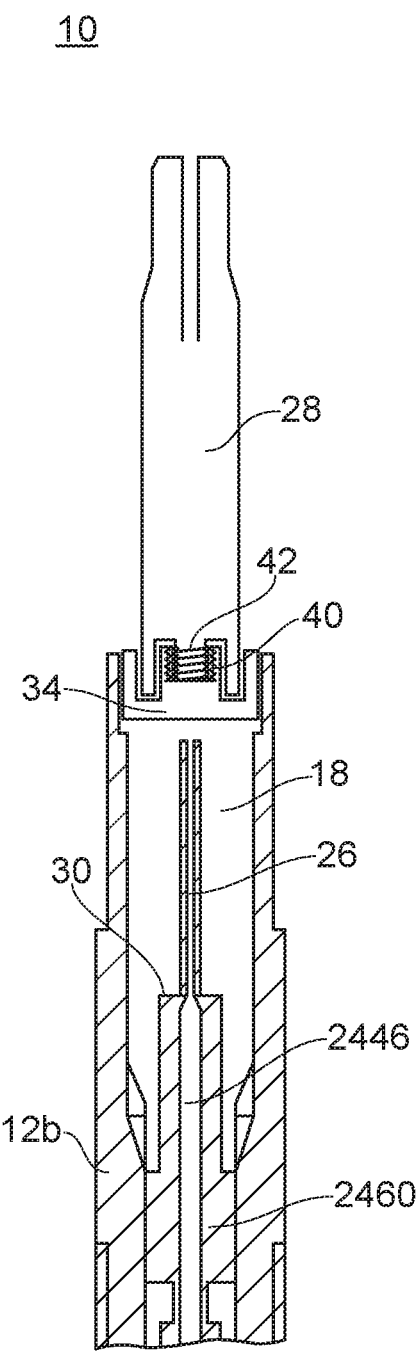
FIGS. 12a and 12b are cross-sectional side view illustrations of the dispenser of FIG. 11 during a process for removing the additional safety cap.
Figure 12B:
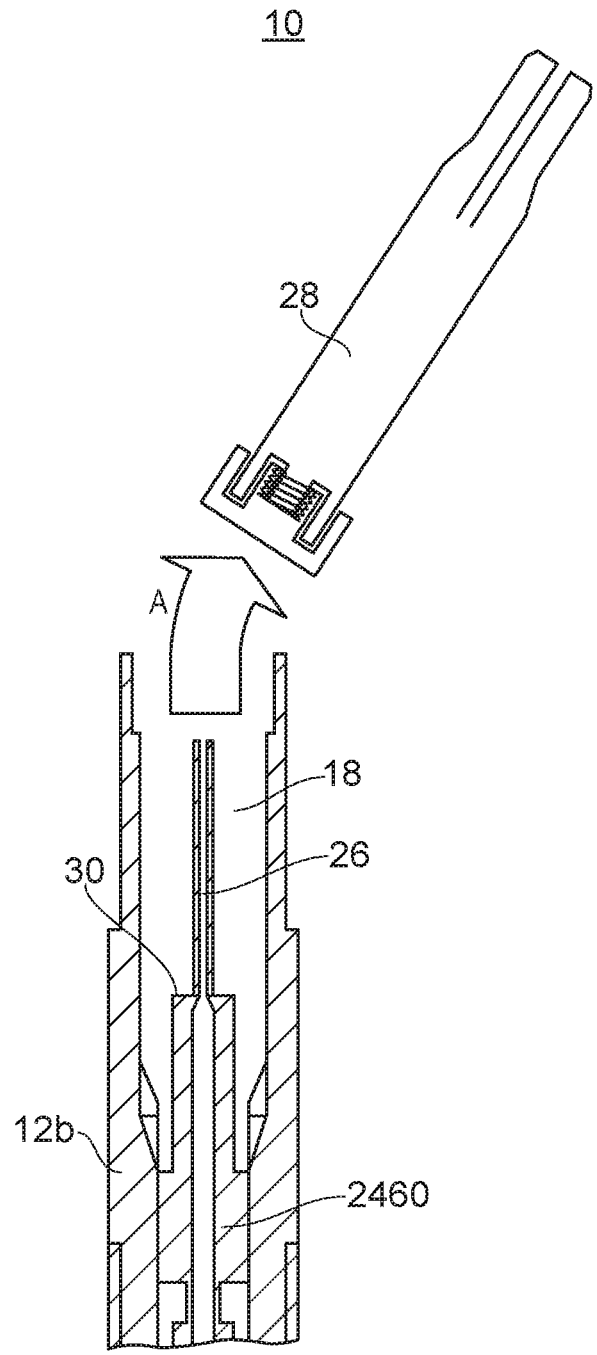

An example of a procedure for removal of the plug 34 from the open ended tube 18 is illustrated in FIGS. 12*a* and 12*b* and is described below.

FIGS. 12*a* and 12*b* illustrate an expanded view of the aperture-end of the dispenser 10 and also illustrate a removal device (i.e. a container to be filled). In the illustrated examples of FIGS. 12*a* and 12*b*, the container 28 to be filled comprises a cartomiser for an e-cigarette device.

Container (cartomiser) 28 comprises, at a non-mouthpiece end thereof, an engagement formation, which conventionally is for securely and removably coupling the container (cartomiser) 28 to a complementary engagement formation of a battery unit of an e-cigarette device. In the illustrated example, engagement formation comprises a helically threaded shaft 42.

To remove the plug 34 from the open ended tube 18, container (cartomiser) 28 is located so that an end of helically threaded shaft 42 thereof is proximal helically threaded bore 40 of plug 34 such that a thread at the end of the helically threaded shaft 42 begins to engage the thread at the mouth of the helically thread bore 40. Relative rotation of the container (cartomiser) 28 to the dispenser 10 (and thus to the plug 34) causes the helically threaded shaft 42 to move into the helically thread bore 40. Continued relative rotation causes the container (cartomiser) 28 to be tightened onto the plug 34 and thus securely couple the container (cartomiser) 28 to the plug 34.

With the container (cartomiser) 28 securely coupled to the plug 34 (see FIG. 12*a*), the plug 34 can be removed from the open ended tube 18 by exerting a pulling force (see arrow A of FIG. 12*b*) on the container (cartomiser) 28, relative to the dispenser 10, to pull the plug 34 from the open ended tube 18. This exposes the dispense conduit 26 to allow a container refilling operation to take place.

The plug 34 is retained by the container (cartomiser) 28, which may avoid the plug 34 being misplaced when it has been removed from the dispenser 10.

An example of a procedure for refilling a container (from an initial state in which the dispenser is closed by both cap 14 and plug 34, to insertion of the container and "pumping" the container relative to the housing) is illustrated in FIGS. 13*a* to 13*h* and is described below.

Figures 13A, 13B:
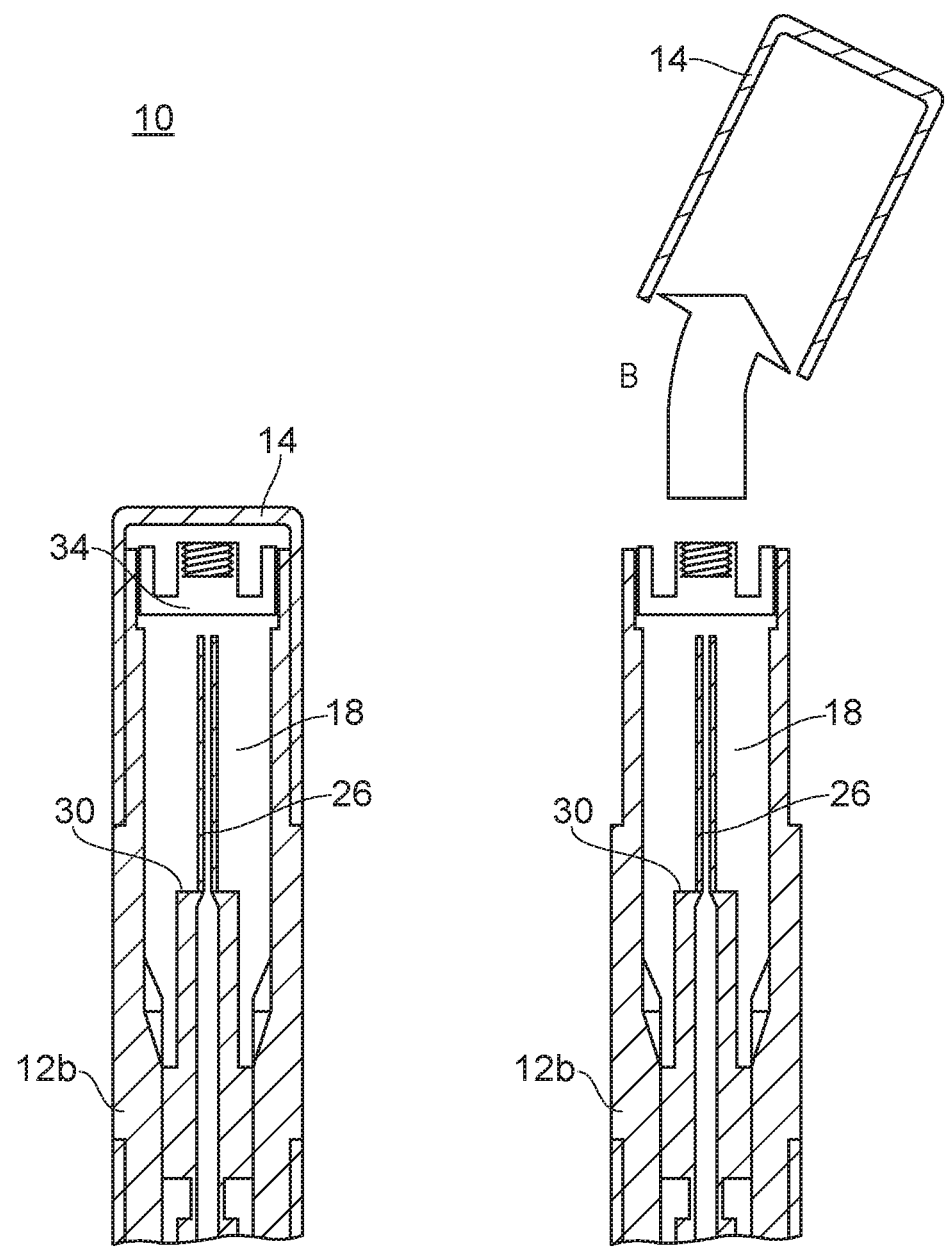
Figure 13C:
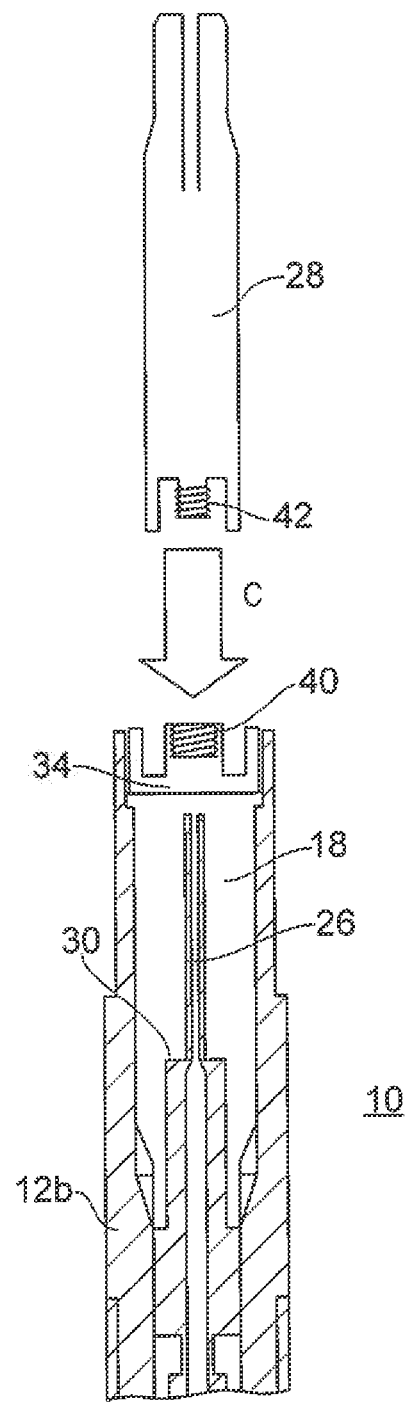

FIG. 13*a* illustrates the dispenser 10 with both the cap 14 and plug 34 in place to close off the open ended tube 18.

Removal of cap 14 (see FIG. 13*b*) is achieved by exerting a pulling force (see arrow B) on the cap 14, relative to the housing 12, to pull the cap 14 from the housing 12. This exposes open ended tube 18, which is closed off by plug 34.

Container (cartomiser) 28 is located so that an end of helically threaded shaft 42 thereof is proximal helically threaded bore 40 of plug 34 such that a thread at the end of the helically threaded shaft 42 begins to engage the thread at the mouth of the helically thread bore 40. That is, by moving the container (cartomiser) 28 toward the open end of the dispenser 10 in the direction indicated by arrow C of FIG. 13*c*.

Figure 13D:
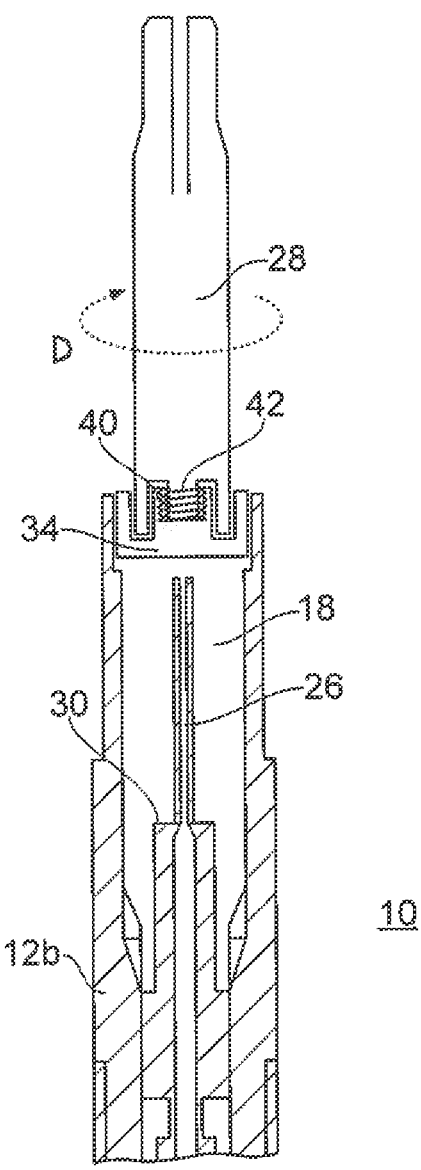
Figures 13E, 13F:
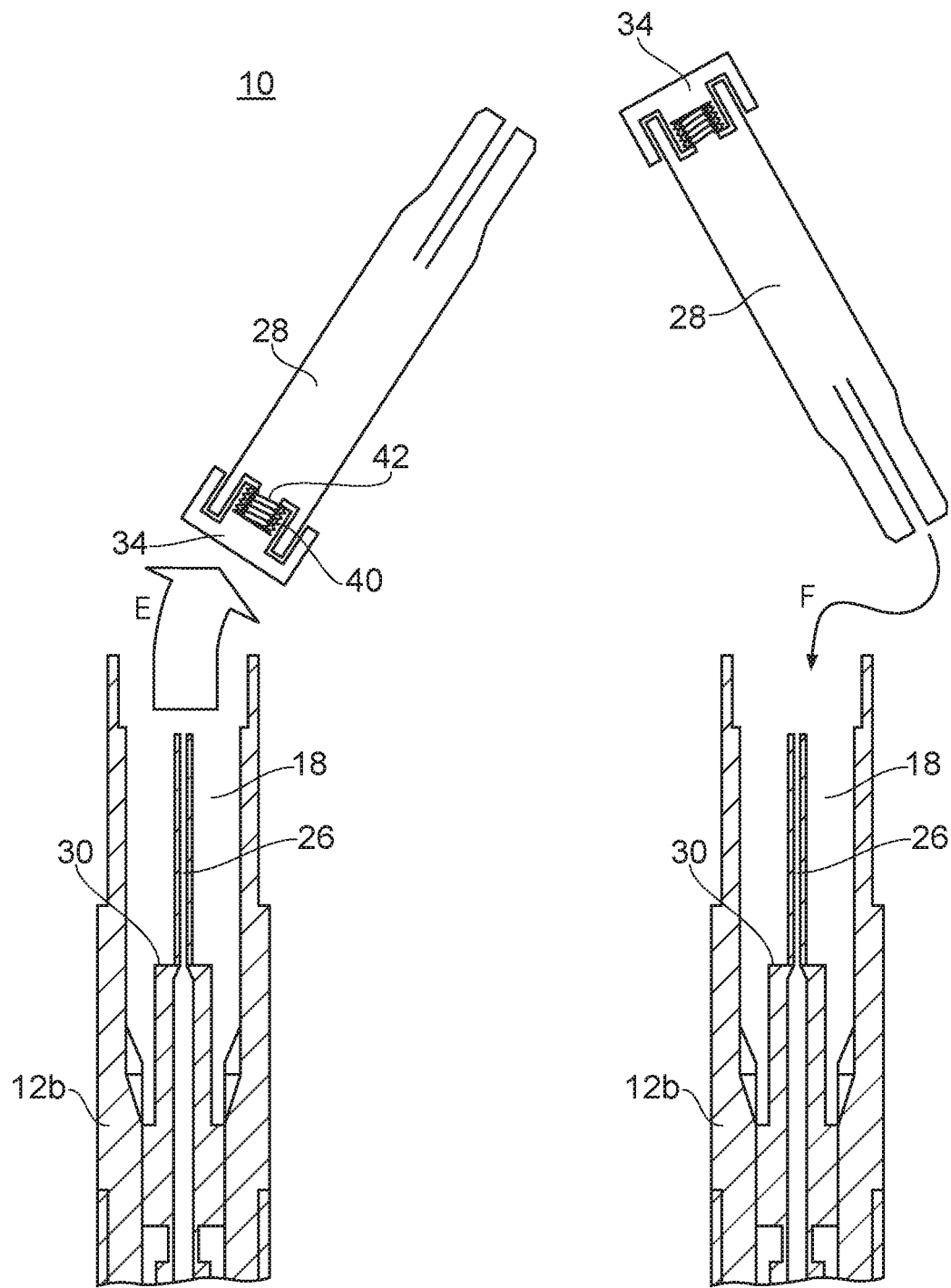

Rotation of the container (cartomiser) 28 relative to the dispenser 10 (and thus to the plug 34) causes the helically threaded shaft 42 to move into the helically thread bore 40 (see arrow D of FIG. 13*d*). Continued relative rotation causes the container (cartomiser) 28 to be tightened onto the plug 34 and thus securely couple the container (cartomiser) 28 to the plug 34.

With the container (cartomiser) 28 securely coupled to the plug 34, the plug 34 can be removed from the open ended tube 18 by exerting a pulling force (see arrow E of FIG. 13*e*) on the container (cartomiser) 28, relative to the dispenser 10, to pull the plug 34 from the open ended tube 18.

Rotation of the container (cartomiser) 28 through 180° (see arrow F of FIG. 13*f*), brings a filling end of the container (cartomiser) 28 to face the aperture of the open ended tube 18. In this orientation, container (cartomiser) 28 can be brought into engagement with the dispenser 10 by moving the filling end of the container (cartomiser) 28 towards the open ended tube 18 (in the direction indicated by arrow G of FIG. 13*g*). Continued movement of the container (cartomiser) 28 relative to the dispenser 10 in the direction indicated by arrow G locates the container (cartomiser) 28 at a position where a filling process can begin.

As described above in relation to FIG. 9, the container (cartomiser) 28 can be filled with liquid contained in the reservoir portion of housing of dispenser 10 by exerting a force on the exposed end of the container (cartomiser) 28 to urge container (cartomiser) 28 from a rest position into the dispenser 10. This action causes an end of the container (cartomiser) 28 within the dispenser to abut the end 30 of the pump arrangement. Continued depression of the container (cartomiser) 28 relative to the dispenser 10 against the action of compression spring within the pump arrangement causes actuation of the pump arrangement until the pump actuator is in a fully depressed position. Actuation of the pump arrangement causes liquid to be communicated via the dispense conduit (not shown), which extends through an aperture of the container 28 into a reservoir thereof, to deliver liquid to the reservoir of the container 28.

Upon release of the depressing force, the compression spring within the pump arrangement urges the container (cartomiser) 28 from the fully depressed position towards the rest position.

The container (cartomiser) 28 can be moved through a number of depression and release cycles (indicated by arrow H in FIG. 13*h*) in order to fill the container (cartomiser) 28.

Figure 14:
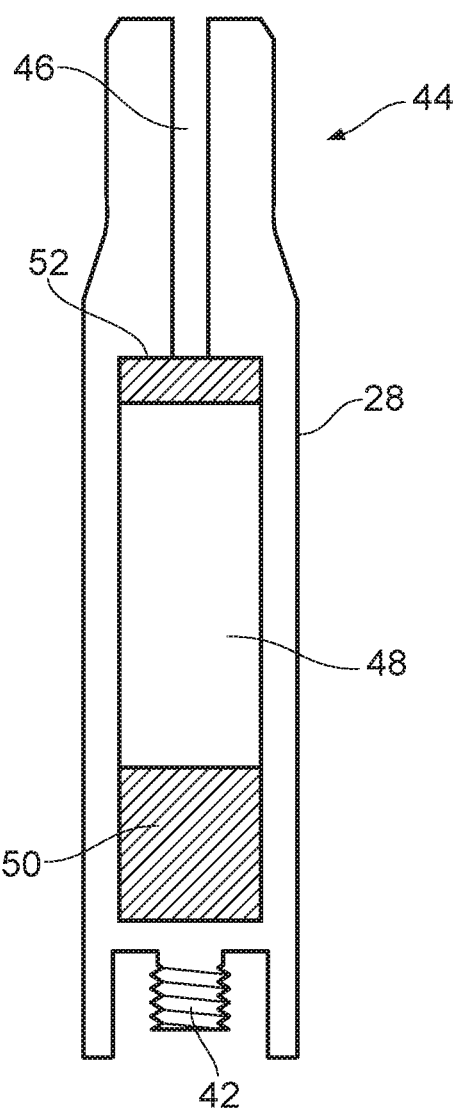
FIG. 14 is a cross-sectional side view illustration of a container according to one or more embodiments of the present invention operative with the dispenser for filling the container.

FIG. 14 illustrates a schematic cross-section side view of a container suitable for use with the dispenser 10. In the illustrated arrangement, the container comprises cartomiser 28, suitable for use in an e-cigarette device.

The cartomiser 28 comprises a mouthpiece end 44 having a conduit 46 that extends into the body of the cartomiser 28. This conduit 46 can receive the dispense conduit 26 therein when the cartomiser 28 is located in the dispenser (during a filling process). The cartomiser 28 further comprises a reservoir 48 for holding a liquid and a heating arrangement 50 in fluid communication with liquid in the reservoir 48.

During operation of an e-cigarette device comprising the cartomiser 28, the heating arrangement 50 vaporises liquid stored in the reservoir 48, and vapour products are dispensed from the cartomiser 28 via conduit 46 (i.e. via a fluid communication path (not shown) that lead from the reservoir to the conduit 46).

The cartomiser 28 further comprises a rupturable membrane 52 configured to sealably close a liquid communication path between the conduit 46 and the reservoir 48. The rupturable membrane 52 does not interfere with the fluid communication path between the reservoir 48 and the conduit 46, such that vapour products created during use bypass the rupturable membrane 52 during passage from the reservoir 48 to the conduit 46 via the fluid communication path.

During a filling process of the cartomiser 28 (using the dispenser 10 described above), the dispense conduit 26 of dispenser 10 pierces material of the rupturable membrane 52 to provide a fluid passage from the dispenser 10 to the reservoir 48 of the cartomiser 28.

Optionally, the rupturable membrane 52 comprises a self-sealing material, for example silicone, which can be pierced by the dispense conduit 26, when the cartomiser 28 is introduced into the dispenser 10, and which can self-seal when the cartomiser 28 is removed from the dispenser 10.

There has been described in the foregoing one or more embodiments of a dispenser that avoids or at least ameliorates the problems of the prior art. More particularly, there is disclosed one or more embodiments of a dispenser that permits the filling and/or refilling of a container without, or at least with reduced, leakage or spillage.

As used herein any reference to "one embodiment" or "an embodiment" means that a particular element, feature, structure, or characteristic described in connection with the embodiment is included in at least one embodiment. The appearances of the phrase "in one embodiment" or the phrase "in an embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention. This description should be read to include one or at least one and the singular also includes the plural unless it is obvious that it is meant otherwise.

In view of the foregoing description it will be evident to a person skilled in the art that various modifications may be made within the scope of the invention.

For example, optionally, the cap 14 may comprise a safety cap. Further optionally, the cap 14 may comprise a child-proof safety cap.

Optionally, the dispenser may be configured to dispense dry power entrained in an air stream to a container to be filled or refilled.

In one or more embodiments of the present invention, the tip of the dispense conduit may be configured to pierce a self-sealing skin of a reservoir chamber of a container to be filled during a filling process. When the filling/refilling process is complete, and the dispense conduit is removed from the reservoir chamber of the container, the skin of the reservoir chamber may "heal" to re-seal the chamber. In an optional arrangement, the chamber may comprise a valve such that the filling/refilling process comprises a mechanical filling/refilling arrangement, such as found in refillable cigarette lighters.

Although embodiments accordance with the present invention have been described in which the pump device 20 forms an end of the reservoir portion 12a together with seat portion 12c it will be evident to a person of ordinary skill in the art that the end of the reservoir portion may be formed of a panel merely having an aperture through which intake conduit 22 may pass and not providing a seat portion for the pump device 20. Regardless of whether the pump device 24 is a part of the end panel of the reservoir portion 12a and therefore could be considered as being disposed at an end of the reservoir, the skilled person will understand that the pump device is disposed toward an end region of the reservoir albeit mounted outside and beyond the end of the reservoir portion 12a.

Embodiments in accordance with the present invention have been described with reference to a pump device 20 having a depression and release cycle. As will be evident to a person of ordinary skill in the art a pump device having a single depression/stroke and configured to force air into the reservoir on the downward stroke which in turn forces reservoir contents up the intake conduit 22 toward the pump arrangement 24 may also be utilised.

Optionally, reservoir portion 12a of dispenser 10 may be formed of a transparent material, or may comprise a transparent viewing "window". This allows a fill-level of the dispenser 10 to be observed. In particular, the transparent material may comprise, for example, Tritan™ (a copolyester material manufactured by Eastman Chemical Company of Kingsport, Tenn., USA), or Barex® (manufactured by Ineos of League City, Tex., USA). These materials may be suitable for forming the reservoir portion 12a, because they are known to be suitable for applications where they are in direct food contact and because they are relatively non-reactive with liquids. Likewise, a reservoir of container 28 may be formed of a transparent material, or may comprise a transparent viewing "window". Again, this allows a fill-level of the reservoir of the container 28 to be observed.

Optionally, dispense conduit 26 of dispenser 10 may comprise a hypodermic needle adapted for the dispenser. In particular, dispense conduit 26 may comprise a gauge 19 metal tube (cannula). Further, optionally, the cannula may be blunted to further reduce instances of pinprick or "stick" injury to a user.

The scope of the present disclosure includes any novel feature or combination of features disclosed therein either explicitly or implicitly or any generalisation thereof irrespective of whether or not it relates to the claimed invention or mitigate against any or all of the problems addressed by the present invention. The applicant hereby gives notice that new claims may be formulated to such features during prosecution of this application or of any such further application derived therefrom. In particular, with reference to the appended claims, features from dependent claims may be combined with those of the independent claims and features from respective independent claims may be combined in any appropriate manner and not merely in specific combinations enumerated in the claims.

The invention claimed is:

1. A dispenser for dispensing a liquid into a cartomiser for a smoking substitute device, the dispenser comprising:
   a reservoir for storing a liquid to be dispensed;
   a manually operative pump arrangement disposed at a first end region of the reservoir;

a conduit extending from the pump arrangement to a second end region of the reservoir distal the first end region, the conduit configured for communicating reservoir contents from the second end region to the pump arrangement;

a dispense conduit extending from the pump arrangement and comprising a dispense aperture at an end region thereof, the dispense aperture in liquid communication with the pump arrangement; and an open ended tube extending in a direction away from the pump arrangement and configured to surround the dispense conduit and to receive a mouthpiece portion of the cartomiser, wherein the open ended tube extends to a position such that the open end thereof is at least coterminous with a dispense aperture end of the dispense conduit and actuation of the pump arrangement causes transfer of reservoir contents from the reservoir to the cartomiser through the dispense aperture end of the dispense conduit and the mouthpiece of the cartomiser, wherein the dispenser is further configured to receive a cap to close the open ended tube, wherein an exterior and/or interior wall of said open ended tube is configured for engagement with a portion of said cap, wherein the dispenser further comprises a plug member, a portion of which is configured for engagement with the exterior and/or interior wall of said open ended tube, and wherein said plug member comprises engagement formations configured to receive complementary engagement formations of a removal device, wherein said removal device comprises the cartomiser.

2. A dispenser according to claim 1, wherein the open ended tube extends to a position beyond the dispense aperture end of the dispense conduit.

3. A dispenser according to claim 1, wherein the dispense conduit is configured to interface with a complementary arrangement in the cartomiser to deliver reservoir contents into the cartomiser.

4. A dispenser according to claim 1, wherein the dispense conduit is configured to penetrate into the cartomiser to deliver reservoir contents into the cartomiser.

5. A dispenser according to claim 4, wherein the dispense conduit is configured to pierce a membrane of the cartomiser to protrude into the cartomiser to deliver reservoir contents into the cartomiser.

6. A dispenser according to claim 1, wherein the cap is a child safety cap.

7. A dispenser according to claim 1, wherein said exterior and/or interior wall comprises engagement formations configured for engagement with complementary engagement formations of said cap.

8. A dispenser according to claim 1, wherein said plug member is removable from said dispenser, when engaged to said removal device, by a pulling action exerted on the removal device.

9. A dispenser according to claim 1, wherein the pump arrangement is resiliently biased towards a closed position.

10. A dispenser according to claim 1, wherein the pump arrangement comprises an abutment surface configured to engage with a complementary surface of the cartomiser and wherein application of a force to the abutment surface actuates the pump arrangement.

11. A dispenser according to claim 10, wherein application of the force is against a resilient bias.

12. A dispenser according to claim 1, wherein the open ended tube is profiled so as to guide the cartomiser into engagement with the dispense conduit.

13. A dispenser according to claim 12, wherein the open ended tube is profiled so as to provide a transition fit for engagement of the cartomiser for reciprocal movement of the cartomiser with respect to the open ended tube.

14. A dispenser according to claim 12, wherein an inner wall of the open ended tube is profiled so as to guide the cartomiser.

15. A dispenser according to claim 12, wherein the open ended tube is profiled so as to receive a mouthpiece for a smoking substitute device.

16. A dispenser according to claim 15, wherein the open ended tube is profiled to provide a complementary cross-section for the mouthpiece for the smoking substitute device.

17. A dispenser according to claim 1, wherein a surface of the open ended tube is coated with an antibacterial coating.

18. A dispenser according to claim 1, wherein the pump mechanism dimensions are configured to deliver a measured dose of reservoir contents for a full pump stroke length.

19. A dispenser according to claim 18, configured to provide feedback indicative of reaching a maximum stroke length, wherein the feedback may be one or more of tactile, visual, and audio feedback.

20. A dispenser according to claim 1, wherein the open ended tube is configured with a locking or a positive engagement mechanism configured to permit a reciprocal movement of the cartomiser when engaged therewith.

21. A dispenser according to claim 1, wherein the pump arrangement comprises a locking or positive engagement mechanism, interoperable with a complementary mechanism on the cartomiser to avoid inadvertent separation of the cartomiser from the pump arrangement.

22. A kit of parts for forming an assembly for filling a container, comprising
a dispenser according to claim 1; and
a container operative with the dispenser for filling the container, the container comprising:
a storage cavity for storing reservoir contents dispensed to the container from the dispenser;
an interface formation configured to receive the dispense conduit of the dispenser to open a conduit between the storage cavity and pump arrangement to permit transfer of reservoir contents from the pump arrangement to the storage cavity responsive to actuation of the pump arrangement; and wherein
the interface formation is disposed in an interface section of the container configured to fit to the open ended tube in order for the dispense conduit to engage with the interface formation.

* * * * *